US006867038B2

(12) United States Patent
Liotta et al.

(10) Patent No.: US 6,867,038 B2
(45) Date of Patent: Mar. 15, 2005

(54) ISOLATION OF CELLULAR MATERIAL UNDER MICROSCOPIC VISUALIZATION

(75) Inventors: Lance A. Liotta, Potomac, MD (US); Michael Emmert-Buck, Silver Spring, MD (US); David B. Krizman, Gaithersburg, MD (US); Rodrigo Chuaqui, Las Condes (CL); W. Marston Linehan, North Bethesda, MD (US); Jeffry M. Trent, Rockville, MD (US); Robert F. Bonner, Washington, DC (US); Seth R. Goldstein, Bethesda, MD (US); Paul D. Smith, Annapolis, MD (US); John I. Peterson, Falls Church, VA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 796 days.

(21) Appl. No.: 09/780,234

(22) Filed: Feb. 9, 2001

(65) Prior Publication Data

US 2002/0037269 A1 Mar. 28, 2002

Related U.S. Application Data

(62) Division of application No. 09/364,617, filed on Jul. 29, 1999, now Pat. No. 6,251,467, which is a division of application No. 09/018,596, filed on Feb. 4, 1998, now Pat. No. 6,251,516, and a continuation of application No. 08/544,388, filed on Oct. 10, 1995, now Pat. No. 5,843,657, which is a continuation-in-part of application No. PCT/US95/02432, filed on Mar. 1, 1995, said application No. 09/364,617, is a continuation-in-part of application No. 08/203,780, filed on Mar. 1, 1994, now Pat. No. 5,843,644, said application No. 09/018,596.

(60) Provisional application No. 60/036,927, filed on Feb. 7, 1997.

(51) Int. Cl.[7] .................................................. C12N 5/00
(52) U.S. Cl. ..................... 435/325; 435/29; 435/30; 435/363; 435/1.1; 436/8
(58) Field of Search ................ 435/1.1, 29, 30, 435/325, 363; 436/8

(56) References Cited

U.S. PATENT DOCUMENTS

| | | |
|---|---|---|
| 2,659,981 A | 8/1953 | Beckman |
| 3,989,591 A | 11/1976 | Liotta |
| 4,012,475 A | 3/1977 | Kindel |
| 4,144,760 A | 3/1979 | Schlueter et al. |
| 4,366,245 A | 12/1982 | Lalonde |
| 4,485,706 A | 12/1984 | Disharoon |
| 4,500,509 A | 2/1985 | Kass |
| 4,545,831 A | 10/1985 | Ornstein |
| 4,619,899 A | 10/1986 | Nikitin et al. |
| 4,624,915 A | 11/1986 | Schindler et al. |
| 4,628,026 A | 12/1986 | Gardell et al. |
| 4,635,791 A | 1/1987 | Jackson et al. |
| 4,647,543 A | 3/1987 | Stocker |
| 4,649,109 A | 3/1987 | Perlman |
| 4,663,219 A | 5/1987 | Janocha et al. |
| 4,665,021 A | 5/1987 | Schnaper et al. |
| 4,741,043 A | 4/1988 | Bacus |
| 4,749,868 A | 6/1988 | Hatanaka et al. |
| 4,767,717 A | 8/1988 | Baisden |
| 4,853,262 A | 8/1989 | Horie et al. |

(List continued on next page.)

FOREIGN PATENT DOCUMENTS

| | | |
|---|---|---|
| DE | 1074885 | 2/1960 |
| EP | 0538777 | 10/1992 |
| EP | 539888 A1 | 5/1993 |
| FR | 2659981 | 3/1990 |

OTHER PUBLICATIONS

Vogles et al., New Eng. J. Med., Jul. 14, 1988, vol. 319(2) pp. 75–79.
Kalebic, T. et al., Clin. Expl. Metastasis, 1988, vol. 6(4), 301–318.
Fenoglio–Preiser t al., Arch. Pathol. Lab. Med. Jul. 1987, vol. 111(7) pp. 601–619.
Whetsell, L. et al., Am. J. Hum. Genet, vol. 49 (4 suppl.) 1991, p. 124, #622.
Kimmel, P.L. et al., Kidney Int., Jun. 1993, vol. 43(6) pp. 1347–1352.
Stoelting Marketing Brochuyre, Quixell Automated Cell Selection and Transfer System 1995–1996.
Erlen, BS. et al., Mod Pathol., Sep. 1993, vol. 6 (5) pp. 612–618.
Lataster et al., Biotech. & Histochem., 1991, pp. 93–99, vol. 66(1).
Grody, WW et al., Mod. Pathol.,Nov. 1989, vol. 2(60) pp. 553–568.
Meltzer et a., Nature–Genetics, vol. 1(1) Apr. 1992, pp. 24=28.

Primary Examiner—Leon B. Lankford, Jr.
(74) Attorney, Agent, or Firm—William Michael Hynes; Townsend and Townsend and Crew, LLP

(57) ABSTRACT

A method of microdissection which involves forming an image field of cells of the tissue sample utilizing a microscope, identifying at least one zone of cells of interest from the image field of cells which at least one zone of cells of interest includes different types of cells than adjacent zones of cells, and extracting the at least one zone of cells of interest from the tissue sample. The extraction is achieved by contacting the tissue sample with a transfer surface that can be selectively activated so that regions thereof adhere to the zone of cells of interest to be extracted. The transfer surface includes a selectively activatable adhesive layer which provides, for example, chemical or electrostatic adherence to the selected regions of the tissue sample. After the transfer surface is activated, the transfer surface and tissue sample are separated. During separation, the zone of cells of interest remains adhered to the transfer surface and is thus separated from the tissue sample, the zone of cells of interest may then be molecularly analyzed.

3 Claims, 10 Drawing Sheets

U.S. PATENT DOCUMENTS

| | | |
|---|---|---|
| 4,907,158 A | 3/1990 | Ketter et al. |
| 4,960,224 A | 10/1990 | Boenisch |
| 5,023,172 A | 6/1991 | Djordjevic |
| 5,137,710 A | 8/1992 | Smalley et al. |
| 5,218,645 A | 6/1993 | Bacus et al. |
| 5,225,750 A | 7/1993 | Higuchi et al. |
| 5,235,522 A | 8/1993 | Bacus |
| 5,244,787 A * | 9/1993 | Key et al. |
| 5,252,487 A | 10/1993 | Bacus et al. |
| 5,264,341 A | 11/1993 | Maciak et al. |
| 5,281,517 A | 1/1994 | Bacus et al. |
| 5,428,690 A | 6/1995 | Bacus et al. |
| 5,451,500 A | 9/1995 | Stapleton |
| 5,512,418 A | 4/1996 | Ma |
| 5,843,644 A * | 12/1998 | Liotta et al. |

\* cited by examiner

Colon    Breast

N   T   N   T

ISOLATION OF CELLULAR MATERIAL UNDER MICROSCOPIC VISUALIZATION

This patent application is a divisional of and claims the benefits of U.S. patent application Ser. No. 09/364,617 filed Jul. 29, 1999 )now U.S. Pat. No. 6,251,467 which was a divisional of Ser. No. 09/018,596, filed Feb. 4, 1998 now U.S. Pat. No. 6,251,516 which claims the benefit of U.S. Provisional Application Ser. No. 60/036,927, filed Feb. 7, 1997, Patent Cooperation Treaty Application Ser. No. PCT/ US96/16517, filed Oct. 9, 1996 and now pending and is a CON of 08/544,388, filed Oct. 10, 1995, now U.S. Pat. No. 5,843,657 which is a CIP of Patent Coorperation Treaty Application Ser. No. WO 95/23960 (PCT/US95/02432), filed Mar. 1, 1995 and now pending, which is CIP of 08/203,780, filed Mar. 1, 1994, now U.S. Pat. No. 5,843,644, the disclosure of which is incorporated by reference.

TECHNICAL FIELD

The present invention relates to methods and devices for the molecular analysis of cellular samples. More particularly, the present invention relates to methods and devices for the microdissection and molecular analysis of cellular samples which may be used in combination with a number of different technologies that allow for analysis of proteins, such as enzymes, and mRNA and DNA from substantially pure populations or subpopulations of particular cell types.

BACKGROUND ART

Many diseases are now understood at the molecular and genetic level. Analysis of such molecules is important for disease diagnosis and prognosis. Previous methods for direct extraction of cellular tissue material from a tissue sample are limited because the extraction reflects only the average content of disease associated markers. In reality, tissues are very heterogeneous and the most diagnostic portions of the tissue may be confined to a few hundred cells or less in a lesion.

Normal tissue samples contain a variety of cell types surrounding and adjacent to the pre-invasive and invasive tumor cells. A region of the tumor tissue subject to biopsy and diagnosis as small as 1.0 mm can contain normal epithelium, pre-invasive stages of carcinoma, in-situ carcinoma, invasive carcinoma, and inflammatory areas. Consequently, routine scraping and cutting methods will gather all of these types of cells, and hence, loss of an allele will be masked by presence of a normal copy of the allele in the contaminating non-malignant cells. Existing methods for cutting away or masking a portion of tissue do not have the needed resolution. Hence the analysis of genetic results by those previous methods are always plagued by contaminating alleles from normal cells, undesired cells or vascular cells.

The molecular study of human tumors is currently limited by the techniques and model systems available for their characterization. Studies to quantitatively or qualitatively assess proteins or nucleic acid expression in human tumor cells are compromised by the diverse cell populations present in bulk tumor specimens. Histologic fields of invasive tumor typically show a number of cell types including tumor cells, stromal cells, endothelial cells, normal epithelial cells and inflammatory cells. Since the tumor cells are often a relatively small percentage of the total cell population it is difficult to interpret the significance of net protein or nucleic acid alterations in these specimens.

Studies of human tumor cells in culture do not account for the complex interactions of the tumor cells with host cells and extracellular matrix, and how they may regulate tumor cell protease productivity or activation. Immunohistochemical staining allows one to examine enzyme distribution in regions of tumor invasion, however, results vary with tissue fixation and antibody-antigen affinity, and provide only a semi-quantitative assessment of protein levels. Furthermore, quantitative interpretation of staining results is complicated by the variability of staining patterns within tissue sections, subjective evaluation of staining intensity, and the difficulty in interpreting the significance of stromal staining. In addition, many antibodies utilized in the study of proteases do not differentiate pro-enzyme from active enzyme species. Assays of enzyme or mRNA levels from homogenates of human tumors does not account for either the mixed population of cells within the specimens, or the concomitant pathophysiologic processes which may be occur in the tissue Prior methods of study have not allowed investigators to specifically examine genetic alterations in pre-invasive lesions. Even the most sophisticated genetic testing techniques to date have been of limited value because the input DNA, RNA or proteins to be analyzed are not derived from pure cell populations exhibiting the disease morphology. Several methods have been reported for tissue microdissection to address this problem, including gross dissection of frozen tissue blocks to enrich for specific cell populations, irradiation of manually ink stained sections to destroy unwanted genetic material, touch preparations of frozen tissue specimens and microdissection with manual tools. These methods, however, are not sufficiently precise and efficient for routine research or high throughput clinical molecular diagnostic applications. Manual microdissection, for example, has good precision but is time consuming, labor intensive, requires a high degree of manual dexterity, and is not generally suitable for the ordinary technologist.

The present inventions provides a novel improved means to specifically examine genetic alterations in pre-invasive lesions of common epithelial tumors such as breast and prostate carcinoma. In particular, the present invention permits the microsampling of as few as one cell, with RNA and DNA extraction of the sampled cell. This method has been demonstrated to be extremely sensitive and to surpass previous and current technologies by more than two orders of magnitude. It has allowed the sensitive detection of loss of heterozygosity in early pre-invasive lesions being a gateway to the discovery of, for example, new genetic loci on chromosome 11 for breast cancer and a new genetic loci on chromosome 8 for prostate carcinoma.

The practice of the invention further permits the construction of genetic libraries from the extracted material. Thus, libraries from predetermined cells of interest, particularly abnormal cells, may be constructed and compared to libraries made from close-by, or adjacent, other cells, such as normal cells. Such libraries may be used, for example, to compare one or more specific genetic loci, the expression of one or more RNAs, particularly mRNAs, to isolate and/or clone one or more specific nucleic acid, and the like.

SUMMARY OF THE INVENTION

It is accordingly one object of the present invention to provide a method of identifying specific cells in cellular tissue sample.

Another object of the present invention is to provide a method of direct extraction of specific cells from a cellular tissue sample.

It is a further object of the present invention to provide an automated method of identifying specific cells in cellular tissue sample.

A further object of the present invention is to provide an automated method of direct extraction of specific cells from a cellular tissue sample.

A still further object of the present invention is to provide a method of obtaining pure cell populations from a cellular tissue samples.

According to these and further objects of the present invention which will become apparent as the description thereof proceeds, the present invention provides for a method of direct extraction of cellular material from a tissue sample which involves:

a) providing a slide-mounted tissue sample;
b) forming an image field of cells of the tissue sample utilizing a microscope;
c) identifying at least one zone of cells of interest from the image field of cells, the at least one zone of cells of interest including different types of cells than adjacent zones of cells; and
d) extracting the at least one zone of cells of interest from the tissue sample.

In another embodiment, the present invention provides a method of direct extraction of cellular material from a tissue sample which involves:

a) providing a tissue sample;
b) contacting the tissue sample with a selectively activatable surface which can be activated to provide selective regions thereof with adhesive properties;
c) identifying at least one portion of the issue sample which is to be extracted;
d) selectively activating a region of the transfer surface which corresponds to and is in contact with the at least one portion of the tissue sample so that the activated region of the transfer surface selectively adheres to the at least one portion of the tissue sample; and,
e) separating the transfer surface from the tissue sample while maintaining adhesion between the activated region of the transfer surface and the at least one portion of the tissue sample such that the at least one portion of tissue sample is extracted from the remaining portion of the tissue sample.

In a preferred embodiment, the activation of the selectively activatable surface is accomplished with a laser.

DESCRIPTION OF THE SPECIFIC EMBODIMENTS

The present invention is directed to a method of analyzing cellular material on a molecular or genetic level which involves: visualizing a field of cells in a tissue sample under a microscope, contacting an identified area with a surface which simultaneously dissolves, extracts and/or retains the cellular material of interest, and transferring the cellular material of interest to a suitable analysis system. The present invention is particularly applicable to the analysis of local tissue polypeptides proteins, such as enzymes and antigens, as well as DNA, RNA, particularly mRNA, lipids, carbohydrates, and other biological molecules and assemblies thereof.

According to one embodiment, the present invention is directed to adhesive transfer methods which involve microscopic visualization and transfer of cellular material to a procurement or transfer surface.

The present invention is also directed to a fully automated system whereby a tissue can be visualized, for example, on a screen, so that a precise field of cells of interest can be identified, for example, by a variety of labels, histochemical stains, antibodies, etc., circumscribed or their location otherwise demarcated, and then be extracted and analyzed, either manually or automatically, or by a combination of the two.

Figure 1:
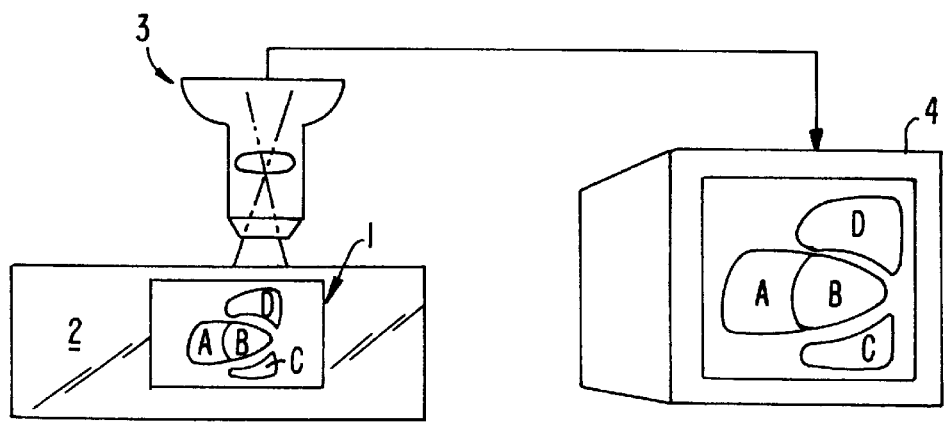
FIG. 1 is a functional system diagram depicting how a tissue sample is microscopically imaged, displayed on a display monitor, and how a region of the imaged sample is selected and identified for subsequent microdissect on and analysis.

FIG. 1 is a functional system diagram which shows how a tissue sample is microscopically imaged, displayed on a display monitor, and how a region of the imaged sample is selected and identified for subsequent microdissection and analysis. As depicted in FIG. 1, a tissue sample 1 is provided on a surface, such as a glass slide 2, for microscopic examination and imaging. The sample tissue 1 can be fixed on the glass slide 2 according to any conventional method, including attachment to the glass slide 2 with an agarose gel, fixing the tissue sample in paraffin, etc.

The glass slide 2 having the sample tissue 1 mounted thereon is placed on the stage of a microscope. The microscope, generally indicated by reference numeral 3, receives an image of the tissue sample 1. An imaging device, such as a video camera, (not shown) is connected to the microscope 3. The imaging device receives the image of the sample tissue 1 from the microscope 3 and displays the image of the tissue sample on an imaging display device, such as display monitor 4.

The image of the sample tissue 1 is limited to the "field" of the microscope 3 for any given image. As indicated in FIG. 1, the field of the sample tissue image may include several zones, "A", "B", "C", and "D" of different types of cells which can be optically distinguished by utilizing a suitable dye(s), labeled molecules such as antibodies or fragments thereof, to stain or otherwise differentiate the predetermined cells of interest in the tissue sample. For exemplary purposes, FIGS. 1 and 2a–2c assume that zone "B" is the zone of cellular material of interest. The image on the display monitor 4 is used by the operator to select and identify one or more zones of the tissue sample 1 which are of interest. According to one embodiment of the present invention, after the zone(s) of interest are selected and identified, the operator manually manipulates a device to extract the identified zone(s) from the glass slide 2. The identification of the cells of interest may also be done automatically through image analysis software. The extracted zone(s) of sample material may include an analysis sample. Otherwise, the identified and extracted zone(s) can include zones which are discarded and the remaining zone(s) which are retained on the glass slide 2, to be later analyzed.

In addition to the manual operation which is discussed in more detail below, it is possible, according to another embodiment of the present invention, to utilize the image on the display monitor 4 to select and identify a sample zone(s) whose relative position is determined by utilizing a computer which receives a digitized signal of the image from the video camera (or microscope), and which receives a reference position of the stage of the microscope 3 upon which the sample is held.

In this automated embodiment of the invention, the computer which performs the positioning detection and recognizing can also be used to control movement of the devices discussed below that are used to extract tissue zones, thus automating the sample removal. In addition, the image of the sample can be electronically scanned to automatically identify zones having a predetermined feature, such as a relevant degree of staining, using known techniques and devices. Thus, in a preferred embodiment, a computer could be used to select and identify zones of interest and the relative position of such zones, for manipulating a device to remove such zones in a completely automated manner.

Figure 2A:
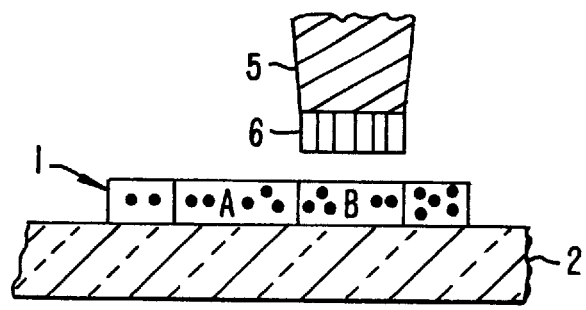
FIG. 2a–2c are a series of functional system diagrams which depict how a zone of tissue sample is extracted from the slide-mounted tissue sample according to one embodiment of the present invention.
Figure 2B:
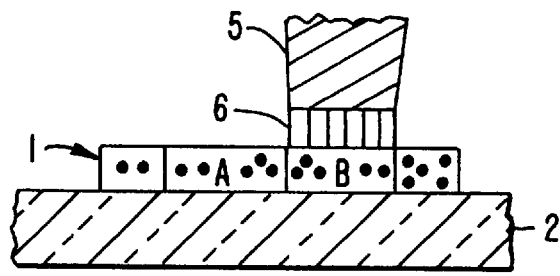
Figure 2C:
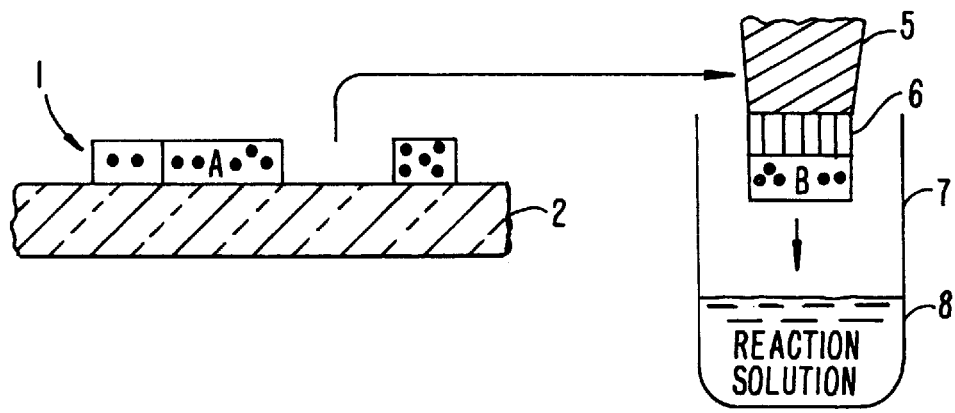

FIGS. 2a–2c are a series of functional system diagrams which show how a zone of tissue sample 1 is extracted from the slide-mounted tissue sample 1 according to one embodiment of the present invention. It is to be understood that the steps depicted in FIGS. 2a–2c could be either preformed manually by an operator or by a computer utilizing conventional positioning and control methods, e.g. computer controlled robotics.

The embodiment of the invention depicted in FIGS. 2a–2c utilize a contact probe 5 which has an adhesive/extraction reagent 6 on the tip thereof. A suitable adhesive/extraction reagent can include a mixture of piccolyte and xylene. In FIG. 2a, the contact probe 5 is positioned either manually or by computer control so as to be above and aligned with the sample zone ("B") to be extracted. As can be readily understood from FIG. 2a, the surface area of the contact probe tip (and adhesive/extraction reagent) needs to be about equal to, and no greater than, the surface area of the zone to be extracted. Otherwise, excessive removal of adjacent tissue zones will occur. Manufacture of probe tips of the required size is well within the capabilities of those skilled in the art.

Once the tip of the contact probe 5 is aligned with the sample zone ("B") to be extracted, the contact probe 5 is lowered so that the adhesive/extraction reagent 6 on the tip thereof contacts the sample zone (FIG. 2b). Of course, depending on the specifics of the apparatus, the probe 5 is raised or otherwise moved into contact with the sample zone of cells of interest.

The adhesive/extraction reagent 6 is selected to readily adhere to the sample zone. Once the adhesive/extraction reagent 6 on the tip of the contact probe 5 contacts the sample zone (FIG. 2b) and the sample zone becomes adhered thereto, the contact probe 5 can be retracted from the contact position (illustrated in FIG. 2b) and moved as shown in FIG. 2c. Since the relative adhesive force of the adhesive/extraction reagent is greater than the adhesive force used to mount the sample on the glass slide, the contact probe 5 pulls the sample zone "B" from the glass slide when withdrawn or retracted.

According to one embodiment of the present invention, a glass pipette was used as the contact probe 5. In this embodiment, the tip of the glass pipette was coated with a solution of piccolyte (568 g/l) and xylene (437.5 g/l) by dipping the tip of the glass pipette in a piccolyte/xylene solution.

In addition to removing the sample zone from the glass slide 2, the contact probe 5 can be used to transfer the extracted sample zone to an analysis container 7 as indicated in FIG. 2c or to any other location, such as a waste container, a culture media, etc. In a preferred embodiment, the contract probe 5 is used to transfer the extracted sample zone to the sample receiving stage of an automated clinical analyzer which is designed to preform a desired analysis of the sample zone. It thus should be understood that the present invention can provide a fully automated method for identifying sample zones on a sample on a surface such as a slide, removing sample zones of interest from the surface-mounted sample, and transporting the extracted sample zones to an automated analyzer which can perform automated analysis of the extracted sample zones. Such analysis can include, for example, analysis of cellular DNA, RNA, proteins, polypeptides, lipids, carbohydrates, and combinations and aggregates thereof.

In FIG. 2c the extracted sample zone is depicted as being dispensed in a container 7 which, for example, can be a test tube or similar container in which analysis on the extracted sample zone can be initiated or performed. As depicted in FIG. 2c, a reagent solution 8 which removes all or a desired component of the extracted sample zone from the contact probe tip can be placed in the container 7 before the extracted sample zone is deposited therein. For example, in the case of DNA analysis, a solution of Tris (50 mM, pH8.5), EDTA (1 mM), Tween 20 (0.5%), and proteinase K (0.2 mg/mL) can be used. This solution extracts the sample zone from the tip of the contact probe 5 and dissolves the tissue material for analysis purposes.

In addition to the contact probe depicted in FIGS. 2a–2c, a hollow suction probe could also be used to extract sample zones from the slide-mounted tissue sample 1. Such a suction probe could be provided with sharp annular tip by which sample zones could be punched out and extracted by suction forces.

Figure 3:
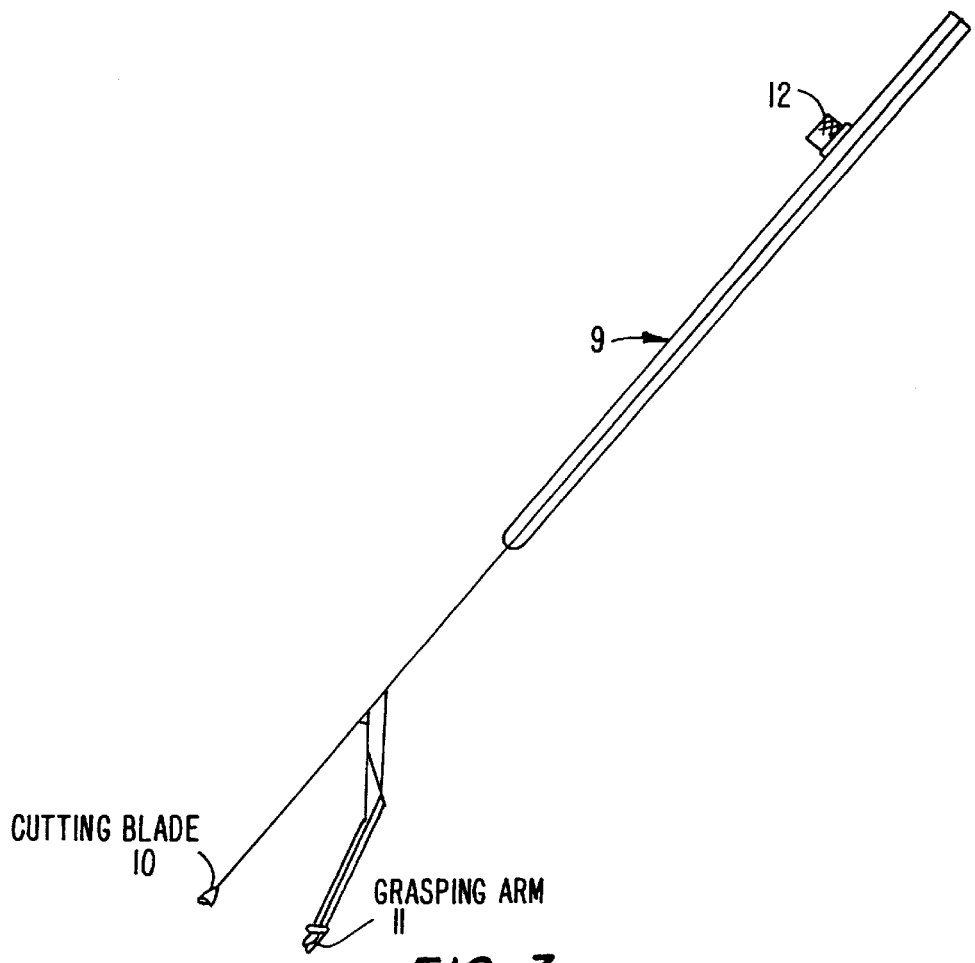
FIG. 3 is a schematic illustration of an alternative device for extracting sample zones from the slide-mounted tissue sample.

FIG. 3 is a schematic illustration of an alternative device for extracting sample zones from the slide-mounted tissue sample 1. The extraction device 9 shown in FIG. 3 includes a cutting blade 10 and a grasping arm 11. The grasping arm 11 can be moved in an opposed manner with respect to the cutting blade 10. The grasping arm 11 is shown in its open position in FIG. 3. The grasping arm 11 is movable between the illustrated open position to a closed position in which the tip of the grasping arm 11 contacts the cutting blade 10. The movement of the grasping arm 11 can be controlled by a cable and pulley system in which grasping arm 11 is caused to pivot at its base by applying tension to a cable which passes through a pulley located at the base of the grasping arm 11. The tension on the cable can be applied by actuating a lever or depressing a button 12 on the device which applied tension to the cable in a known manner. Such actuating mechanical structures are known in the art of gripping devices.

In operating the device of FIG. 3, the cutting blade 10, which is at an obtuse angle with respect to the central axis of the device can cut out and scoop up a portion of a tissue sample by placing the cutting blade 10 on one edge of a portion of the tissue sample to be extracted and then moving the grasping arm 11 into the closed position. As the grasping arm 11 comes into contact with the tissue sample, it draws the cutting blade 10 into the sample and presses a portion of the sample toward the cutting blade 10 thereby causing a portion of the sample contacted between the cutting blade 10 and the grasping arm 11 to be cut out and scooped up from the sample.

In a further, alternative embodiment of the device of FIG. 3, the movement of the grasping arm 11 can be effected by a toothed gear instead of a pulley and a cooperating toothed rod in place of a cable. Additional such mechanical structures are known in the art of gripping devices.

Figure 4B:
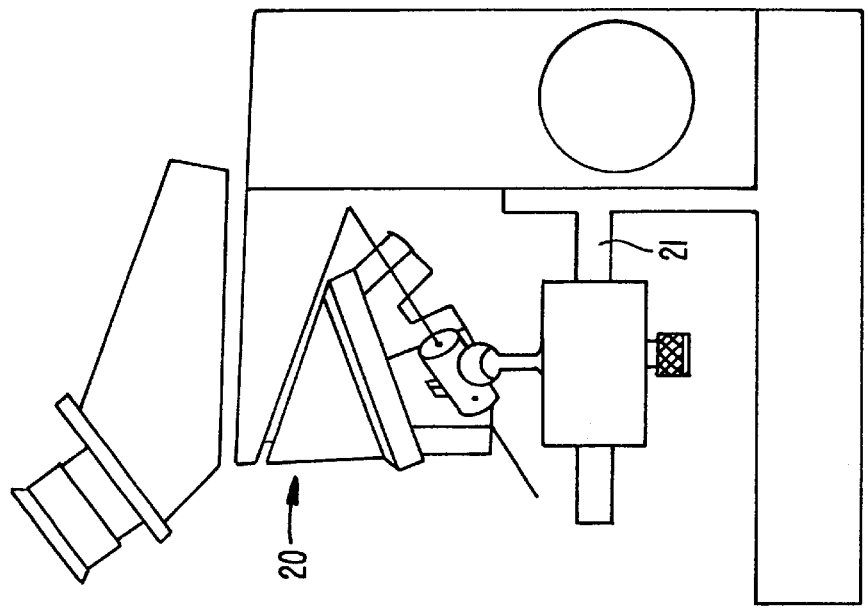
FIGS. 4a and 4b are schematic diagrams of a manual extraction tool manipulator which can be used together with the extraction device of FIG. 3 according to the present invention.
Figure 4A:
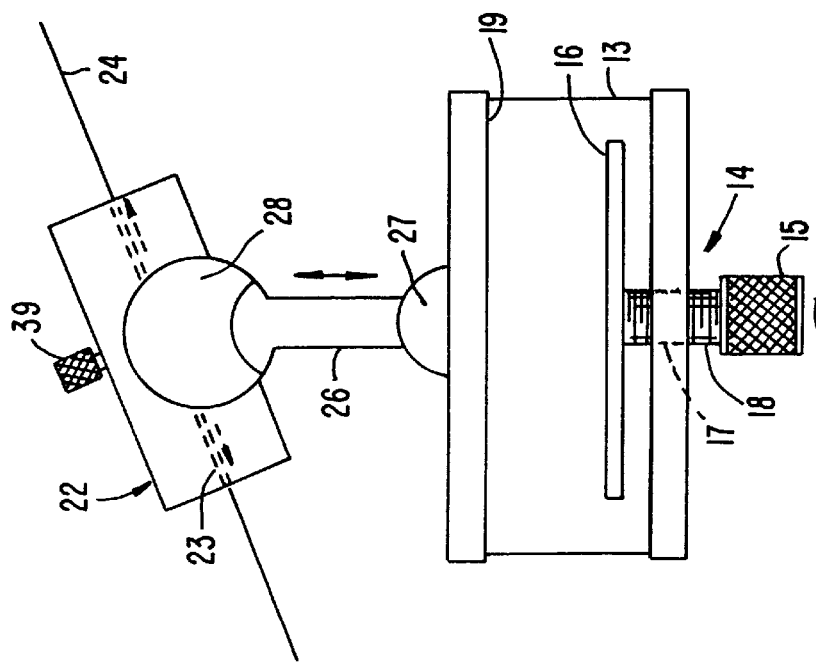

FIGS. 4a and 4b are schematic diagrams of a manual extraction tool manipulator which can be used together with the extraction device of FIG. 3 according to the present invention. In FIG. 4a, the extraction tool manipulator is depicted as having a base 13 equipped with a clamping means 14 for removably attaching the device to a brace or support portion of the stage of a microscope (see FIG. 4b). The clamping mechanism includes a clamping plate 15 that is secured to a threaded shaft 16 which passes through a threaded bore 17 in a lower portion of the base 13. A tightening knob 18 is provided on the end of the threaded shaft 16. Turning the tightening knob 18 causes the clamping plate 15 to move with respect to an upper portion 19 of the base 13. Thus, the extraction tool manipulator can be clamped to a portion of the stage of a microscope 20 as depicted in FIG. 4b by positioning a brace or support portion 21 of the stage of the microscope 20 between the clamping plate 15 and the upper portion 19 of the base 13 and turning knob 18 to tighten the clamping plate 15 against the brace or support portion 21 of the stage of the microscope 20.

The extraction tool manipulator includes a tool holder 22 having a through-bore 23 therein for receiving the shaft of an extraction tool 24. Ideally, the tool holder 22 should allow for damped fore and aft movement of the extraction tool. Therefore, according to a preferred embodiment, the through-bore 23 of the tool holder 22 contains a bushing which can be adjustably tightened against the tool shaft by tool locking screw 39.

The tool holder 22 is supported by support shaft 25 which is connected at opposite ends by substantially 360° damped swivels 26 and 27 to the tool holder 22 and the base 13. The length of the support shaft 25 between the 360° damped swivels 26 and 27 is adjustable. The adjustment of the independent 360° damped swivels 26 and 27 together with the adjustable length of the support shaft 25 and the position of the tool shaft within through-bore 23, allows a high degree of movement of the extraction tool with respect to a slide-mounted sample positioned on the stage of the microscope. Therefore, an operator can manipulate an extraction tool held by the extraction tool manipulator and remove selected tissue zones from a slide-mounted tissue sample with a high degree of precision.

Figure 5:
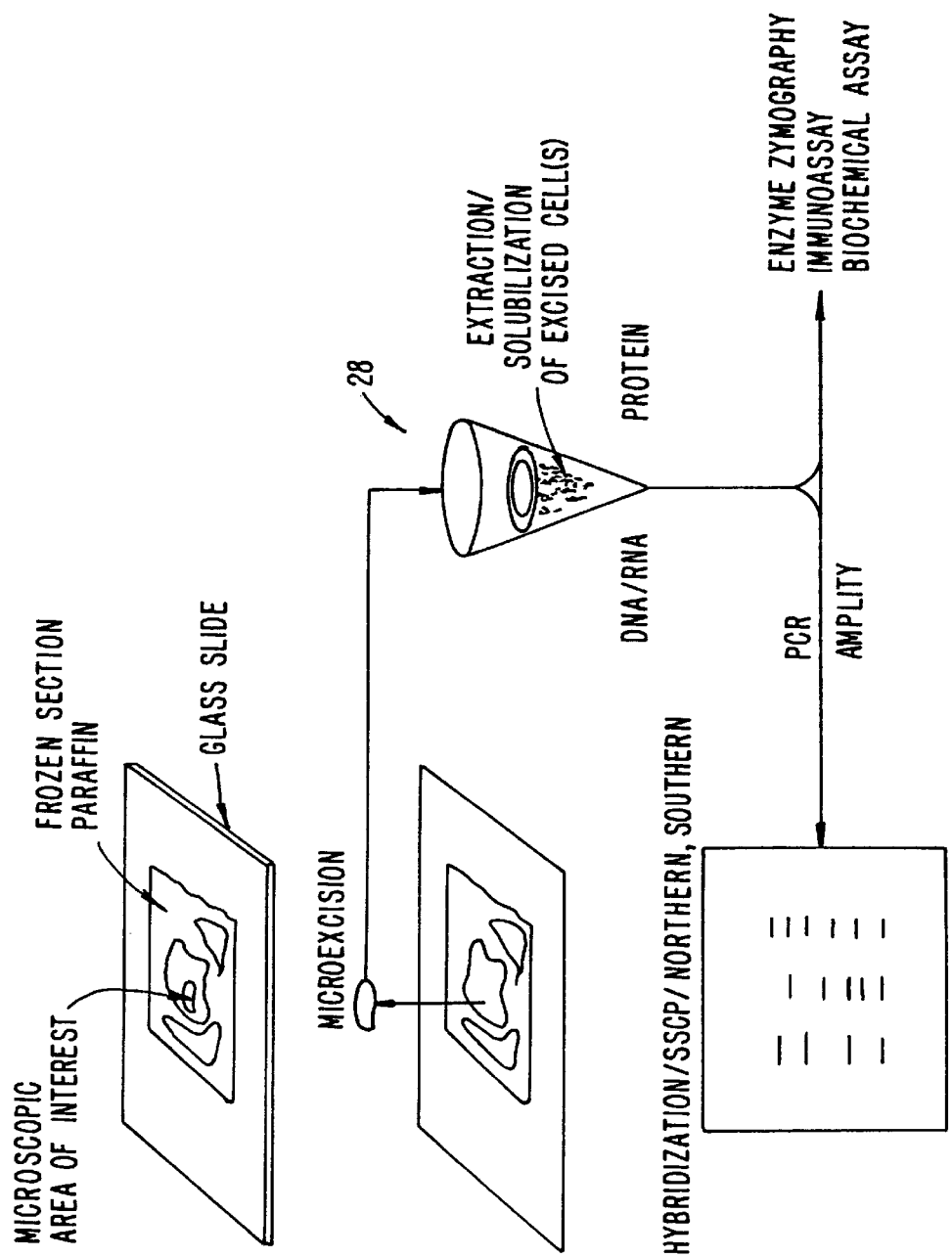
FIG. 5 is a functional system diagram which shows how a zone of sample tissue can be directed to an appropriate analysis protocol.

FIG. 5 is a functional system diagram which shows how a zone of sample tissue can be directed to an appropriate analysis protocol. As depicted in FIG. 5, a microextraction of a zone of tissue sample can be taken from a slide-mounted tissue sample 1 as discussed above and transferred to a sample preparation stage 28 in which the cells of interest can be extracted and collected for analysis. Excised cells may also be solubilized at this stage. If these cells contain, or are suspected to contain, one or more DNA or RNA of interest, the extracted sample may be subjected to polymerase chain reaction (PCR) amplification, followed by, for example, hybridization, strand conformational polymorphism, and southern and northern blotting, sequencing, etc. as desired. Of course, other techniques for analysis of DNA and RNA are known to those skilled in the art and encompassed by the spirit and scope of the invention.

If the extracted cells contain, or are suspected to contain proteins or polypeptides of interest, the extracted sample can be subjected to enzyme zymography, for example using one or more labeled substrates, an immunoassay utilizing, for example, labeled antibodies or functional fragments thereof, a biochemical assay, and the like.

Selective extraction or microdissection of frozen tissue sections according to the present invention allows for recovery and analysis of both active enzymes and mRNA. Additionally, the DNA recovered from these sections is in the native condition and can be used for studies such as DNA fingerprinting. Microdissection of paraffin embedded tissues according to the present invention allows for PCR amplification of DNA, for example, from pure cell populations representing less than one high powered field, or a single layer of epithelial cells lining cystic spaces.

For general preparation of samples for frozen section microdissection according to the present invention, microdissection slides can be prepared by placing 1% agarose on a standard histology slide and cover slipping. After a short period of time, e.g., about 5 minutes, the cover slip is removed leaving a thin gel on the slide. A small frozen tissue section, e.g. about 25 micron thick, is placed on the agarose gel and briefly stained with eosin. The tissue may also be treated with agents to denature or otherwise inhibit RNase depending on the subsequent extraction method. Under direct microscopic visualization, the specific cell population or sub-population of interest is procured from the tissue section utilizing the techniques discussed above.

For enzyme analysis the procured tissue specimen can be placed in an appropriate buffer depending on the enzyme of interest, as known to the person skilled in the art. The enzyme levels can be measured by several methods including zymography and the use of specific substrates, including fluorometric, colorometric and radioactive substrates. The precise levels of enzyme expression in a specific, predefined cell population can be thus determined and, where desired, compared to that of another, independently isolated sample from the tissue sample.

For mRNA analysis the tissue specimen can be placed on agarose and treated with agents to denature or otherwise inhibit RNase, if desired. The procured tissue specimen is immediately frozen in liquid nitrogen. The tissue can be used immediately or stored at −70° C. for several months. The mRNA can be extracted using, for example, column chromatography on oligo-dT (Micro-FastTrack mRNA Isolation Kit, Invitrogen Co.). The recovered mRNA of the pure cell populations can also be amplified and investigated using polymerase chain reaction (PCR) technology, such as, for example, by RT-PCR as known to those skilled in the art.

For DNA analysis the tissue specimen can be placed in a single step extraction buffer solution of 50 mM Tris, pH 8.5, 1 mM EDTA, 0.5% Tween 20, and 0.2 mg/ml proteinase K, incubated for four hours at about 37° C., followed by ten minutes incubation at about 95° C. The recovered DNA can also be amplified and analyzed using PCR technology in combination with analysis techniques, such as blotting, sequencing, etc., known in the art. If native DNA is required for DNA fingerprinting analysis, the proteinase K can be added after DNase in the fingerprinting protocol.

For paraffin section microdissection routine, formalin fixed, paraffin embedded tissue sections are microdissected after de-paraffinization and brief staining with eosin. Tissue sections are visualized by direct microscopy and cell populations or subpopulations of interest are procured using a modified glass pipette with the adhesive coated tip discussed above. Tissue specimens as small as one cell can be procured with this method. The specificity of dissection represents a significant improvement over currently known techniques.

For DNA analysis of paraffin embedded tissue, the glass pipette with the dissected tissue specimen is placed in a single step extraction buffer solution of 50 mM Tris, pH 8.5, 1 mM EDTA, 0.5% Tween 20, and 0.2 mg/ml proteinase K, which removes the tissue from the pipette tip. The sample is incubated, depending on sample size, from two to twenty-four hours at about 37° C., followed by a ten minute incubation at about 95° C. The glass pipette tip can then be sterilized and reused, although this is not generally recommended in the case of PCR-based analysis due to the potential amplification of cross-contaminating materials.

According to the general procedure, an adhesive surface is placed in contact with the surface of the cells or tissue and the adhesive force binds the cellular material of interest to the adhesive surface. The adhesive surface, which can be the tip of a tool or needle, is used to procure the material and transfer it to a liquid analysis reaction mixture. Examples of adhesive surfaces include adhesive coatings on the tip of the tool, or the use of electrostatic forces between the tip and the surface of the cellular material.

As described in detail below, the isolation and transfer methods of the present invention can involve a specialized continuous activatable adhesive layer or surface which is applied to the cellular material over an area larger than the area selected for microscopic procurement. The adhesive function of the subsection of the surface in contact with the area selected for procurement is activated by electromagnetic or radiation means.

FIGS. 8a–8d are schematic illustrations of the sequential steps of an adhesive transfer method according to one embodiment of the present invention.

Figure 8A:
FIGS. 8a–8d are schematic illustrations of the sequential steps of an adhesive transfer method according to one embodiment of the present invention.

As depicted in FIG. 8a, the adhesive transfer method utilizes a transfer surface 30 which includes a backing layer 31 and an activatable adhesive layer 32. In procedures which utilize laser activation of the adhesive layer, the backing layer 31 is preferably transparent, e.g. made of a transparent polymer, glass, or similar material. The activatable adhesive layer 32 can be an emulsion layer, a coated film, or a separate impregnated web fixed to the backing layer. Examples of materials from which the adhesive layer 32 can be made include thermal sensitive adhesives and waxes (e.g., #HAL-2 180C from Precision Coatings), hot glues and sealants (available from Bay Fastening Systems, Brooklyn, N.Y.), ultraviolet sensitive or curing optical adhesives (e.g., N060-N0A81, ThorLabs Inc.), and thermal or optical emulsions (e.g., silkscreen coated emulsion B6 Hi Mesh, Riso Kagaku Corp.)

The backing layer 31 provides physical support for the adhesive surface, and thus can be integrated physically into the activatable adhesive surface.

The activatable adhesive layer 32 is characterized by its ability to be stimulated (activated) by electromagnetic radiation so as to become locally adherent to the tissue. For purposes of selectively activating the activatable adhesive layer 32, one or more chemical components can be incorporated into the layer, which chemical components cause selective absorbance of electromagnetic energy. Preferably, such chemical components are IR-absorbable dyes suitable for use in conjunction with, for example, laser diodes.

As depicted in FIG. 8a, the transfer surface 30 is initially positioned over a cellular material sample 33 which can be a microtome section or cell smear which is supported on a support member 34 such as a microscopic slide. In the case of a tissue microtome, routine procedures can be used to provide paraffin-embedded, formalin-fixed tissue samples.

Figure 8B:
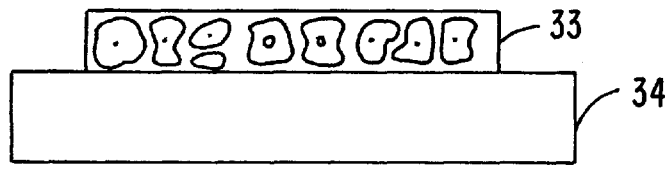

As shown in FIG. 8b, the transfer surface 30 is brought into contact with the cellular material sample 33. It is noted that the activatable adhesive layer 32 preferably has a larger area than the subregion of cellular material sample which is subsequently selected for procurement.

The transfer surface 30 can be fixed to the cellular material sample support 33 by clips, guides, tape, standard adhesives, or similar convenient means. The transfer surface 30 can also contain a label region 35 (see phantom lines in FIG. 8b) to write information such as the patient's identification code or a test designation.

Figure 8C:
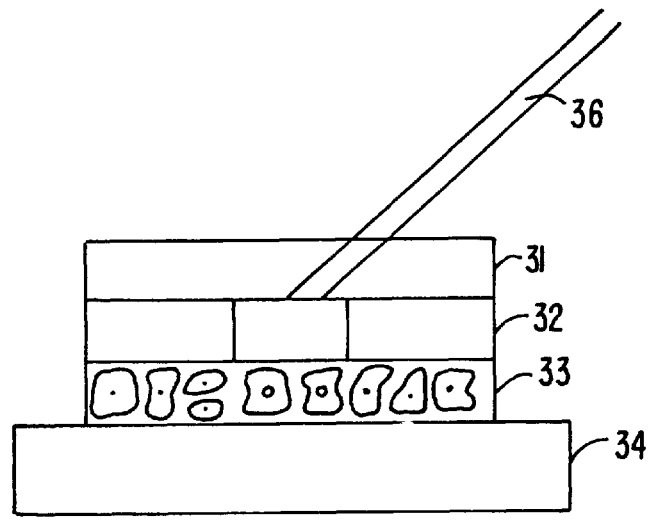

After the transfer surface 30 is brought into contact with the cellular material sample 33, the cellular material sample is viewed by standard low or high power microscopy to locate the region of interest. This region can range in size from an area smaller than a single cell (less than 10 microns), to a few cells, to a whole field of cells or tissue. When the area of interest is identified, the precise region of the activatable adhesive layer 32 which is immediately above the area of interest is activated by a beam of electromagnetic energy 36, e.g., a laser beam, as depicted in FIG. 8c.

Application of the electromagnetic energy 36 causes the region of the activatable adhesive layer 32 which is immediately above the area of interest to adhere to the area of interest. Although FIGS. 8c and 8d depict a single region of interest, it is to be understood that multiple, discontinuous regions of interest could be selected and procured by appropriate aiming and application of the electromagnetic energy.

Figure 8D:
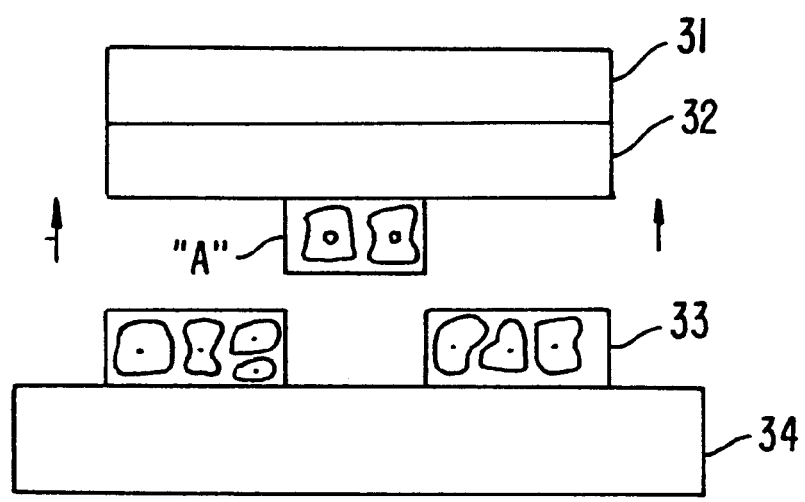

As depicted in FIG. 8d, after one or more regions of interest "A" are identified and the corresponding region(s) of the activatable adhesive layer 32 is activated by a beam of electromagnetic energy 36, the transfer surface 30 is detached from the cellular material sample support 34. As shown, the removed transfer surface 30 carries with it only the precise cellular material from the region of interest "A", which is pulled away from the remaining cellular material sample.

As mentioned above, a single transfer surface can be used to remove a plurality of areas of interest from a single cellular material sample. The transfer surface 30 carrying the procured cellular material can be treated with suitable reagents to analyze the constituents of the transferred material. This can be accomplished by submerging the transfer surface 30, to which the procured cellular material is adhered, in a suitable reagent solution. Alternatively, one or more of the procured cellular material regions can be removed from the transfer surface 30, or portions of the transfer surface 30 to which the procured cellular material are adhered can be punched out of the transfer surface 30 and analyzed separately.

Figure 9:
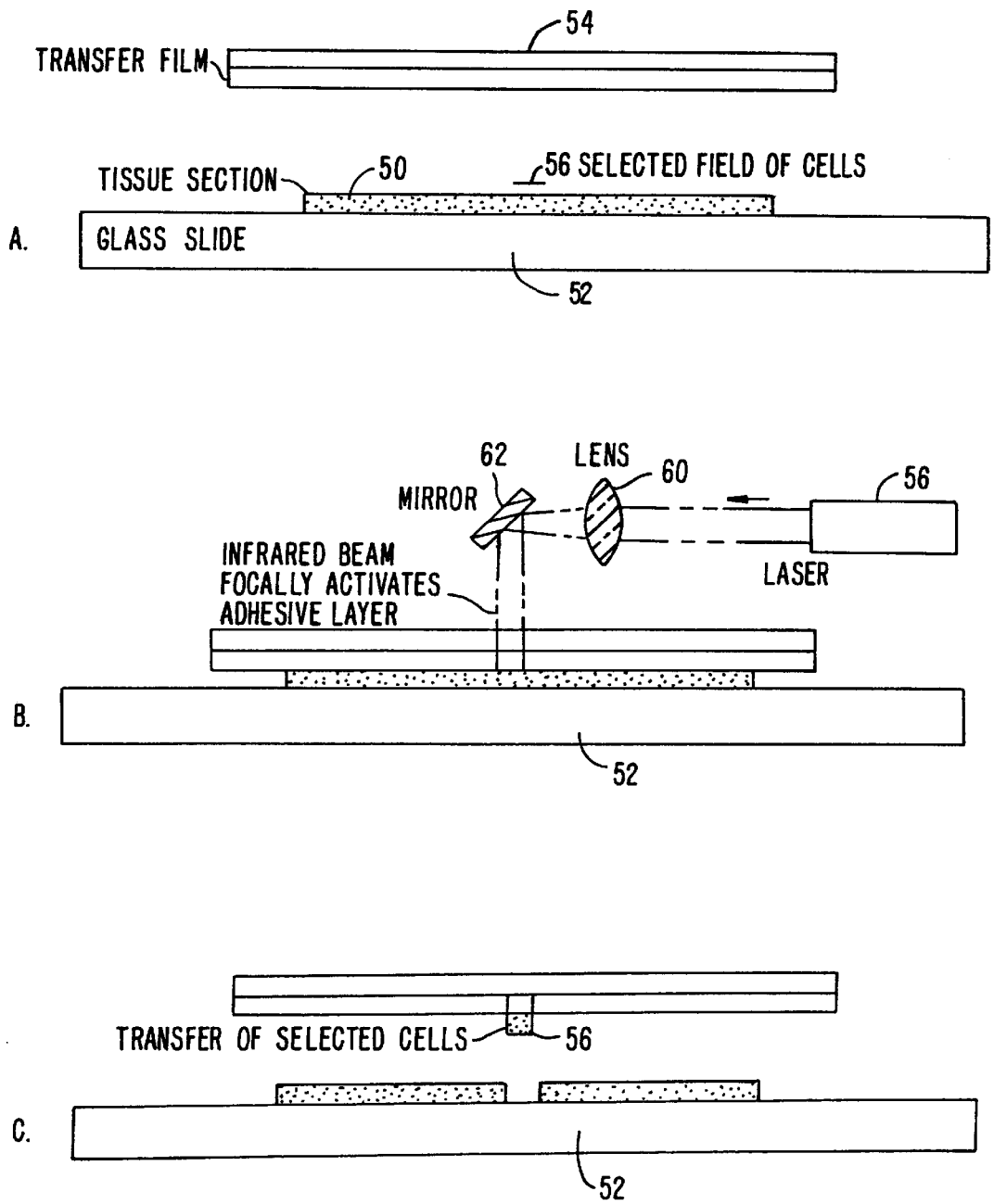
FIG. 9 schematically depicts the laser capture microdissection technique.

In another embodiment of the invention, one or more cells of interest are isolated via laser capture microdissection as schematically depicted in FIG. 9. In this method of the invention, a tissue sample specimen 50 is mounted on a support, such as glass slide 52. As before, a transparent or translucent film or tape 54 (the transfer film) is placed on top of the tissue sample specimen 50. The tissue sample 50 is then examined microscopically for predetermined target cells, such as abnormal cells (or control cells for comparison). As before, the cells may be stained with dye(s), immunologically, etc. to identify and/or differentiate the predetermined cells 56 of interest in the sample. The pre-determined cells of interest 56 are next made to coincide with a target point, wherein electromagnetic radiation may be focused. This coincidence may be accomplished, for example, by x-y-z translation of either the specimen 50 or the target point. For example, the target point may coincide with the center of the imaging field and the microscope stag translated such that the predetermined cells of interest are brought to this target point. One or more focused pulses of energy (e.g., electromagnetic energy in the form of light from a laser) is directed at the film overlying the target. Sufficient energy is directed to the target point so as to preferentially heat or otherwise alter the adhesive characteristics of the film or tape covering the predetermined cells of interest at the target point. In this way, the film or tape 54 is made selectively adhesive at the specific target 56 in the sample by optical activation in precisely predefined locations.

It is preferred that lasers 58 are used in the present invention which, in conjunction with lens 60 and mirror 62 provide electromagnetic energy to the target spot. This is because lasers 58 are high brightness light sources of intense, collimated light that can be readily and efficiently focused to small regions on a given surface. By using a laser focus onto the optical center of the field of view of an optical microscope, activation energy can be supplied to a target region of the film or tape lying on top of the tissue sample. Moreover, the timing and duration of lasers are readily controlled, such that a controlled amount of energy can be directed to the target spot. Additionally, a laser beam can be focused to spots as small as the diffraction limit of the wavelength used and thus permit selective adhesion to targets as small as one micron. Thus, the spots can be small enough to select a homogenous cluster of cells, an individual cell, or even a portion of a cell.

When sufficient energy from the focused pulse of radiation is absorbed to provide activation of the film surface 54 which is in contact with the predetermined cells of interest in the tissue sample, an adhesive bond is formed between the film or tape 54 and the specifically targeted cells 56. As long as the focal bond strength formed between the film 54 and the targeted tissue 56 is greater than the bond strength for the targeted tissue for the underlying substrate (e.g., microscope slide 52 and the bond strength within the targeted tissue), the targeted tissue 56 can be procured upon the removal of the film.

The size of the tissue transferred, depending upon the needs of the operator, can be varied by changing the diameter of the laser beam and pulse durations. Highly reproducible transfers in the 60 to 700 $\mu$m diameter range are easily attainable for procurement of small (100 $\mu$m to 1 mm) lesions without the encroachment of adjacent, nonneoplastic cells. In most basic and clinical research studies, procurement of several hundred to several thousand cells is necessary to provide sufficient genetic material for reliable amplification and statistically meaningful analysis. However, since laser beams can be focused to less than a one cell diameter, transfers of targeted single cells or even parts thereof is thought possible under the practice of the invention.

Thermoplastic polymer films are widely used as heat and pressure activated adhesives for bonding surfaces. Most of these polymer films are transparent or translucent to visible light used in conventional light microscopy. These films are, however, strongly absorptive in specific regions of the electromagnetic spectrum (e.g., in regions of the infrared associated with strong molecular vibration modes such as 3000, 1800, 1400–960 $cm^{-1}$)

The transfer film 54 may be made of a wide variety of electromagnetically or thermally activatable materials, such as ethylene vinyl acetate (EVA), polyurethanes, polyvinyl acetates, and the like. Specific other selectively activatable materials found useful in the practice of the invention are: thermal sensitive adhesives and waxes, such as Precision Coatings product #HAL-2 180C; thermally-activated hot glues and sealants, such as those from Ban Fastening Systems (Brooklyn, N.Y.); ultraviolet sensitive or curing optical adhesives, such as ThorLabs, Inc. product N060-N0A81; thermal or optical emulsions, such as silkscreen coated emulsion B6, high mesh powdered, reconstituted lelt fixit emulsion (Riso Kagaku Corp.) and various other compounds including acetal, acrylic, alloys and blends, allyl, bismaleimides, cellulosics, epoxy, fluoroplastics, ketone-based resins, liquid crystal polymers, melamine-formaldehyde, nitrile, nylon, phenolic, polyamide, polyacrylate, polybenzimidazole, polybutylene, polycarbonate, thermoplastic polyester, liquid crystal polymers, polybutylene terephthalate (PBT), polycyclohexvlenedimethylene terephthalate (PCT), engineering grade polyethylene terephthalate (PET), standard grade polyethylene terephthalate (PET), thermoset polyetherimide polyethylene polyester, branched polyethylene, ethylene acid copolymer, ethylene-ethyl acrylate (EEA), ethylene-methyl acrylate (EMAC), ethylene-vinyl alcohol copolymers (EVOH), high-density polyethylene, HMW-high-density polyethylene, Ionomer, linear low-density polyethylene, linear polyethylene, low-density polyethylene, UHMW polyethylene, very low-density polyethylene, thermoplastic polyimide, thermoset polyimide, polymethylpentene, modified Polyphenylene oxide, polyphenylene sulfide, blow molding PPS, polyphthalamide, polypropylene, polypropylene homopolymer, polypropylene impact copolymers, polypropylene random copolymers, silicones, styrenic resins, ADS, ACS, acrylic-styrene-acrylonitrile, expandable polystyrene, general purpose polystyrene, impact polystyrene, olefin-modified SAN, polystyrene, styrene-acrylonitrile (SAN) and styrene-butadiene copolymers.

The adhesive film described above may be self-supporting or laminated with a support film. Additionally, the support film may be made of a material that does not absorb the electromagnetic energy so strongly as to interfere substantially with the activation of the thermoplastic polymer. The support film preferably absorbs weakly, if at all, at the activation wavelength and at the visualization wavelength. The activatable film, on the other hand, preferably absorbs weakly, if at all, at the visualization wavelength but strongly at the activation wavelength. The support film should also be unaffected by the resulting thermal transients occurring during the activation.

It is also possible to add infrared absorbing dyes to the thermoplastic films 54 to provide strong absorption at other specific infrared wavelengths without altering the films transparency to visible light. Such dyes are preferably IR absorbing dyes which are readily soluble in the plastic films and have a very strong, narrow IR or near IR absorption bands that can be matched to a variety of IR or near IR lasers (including particularly laser diodes). If the focused pulse of electromagnetic radiation (e.g., laser) is delivered at wavelengths that are strongly absorbed by the film, then the film may be efficiently focally heated.

Many dye types could be considered for IR absorption, since most classes of visible absorbing dyes can be extended in wavelength by molecular modification. Phthalocyanines and cyanines have been among the most popular dyes because of stability, ease of preparation, solubility, optical and other properties. Moreover, the number of possible modifications of these dyes is very large because various central metal atoms which can be added and a variety of ring attachments which can be made to them. A book which gives a general overview of IR absorbing dyes is:

INFRARED ABSORBING DYES

Masaru Matsuoka, ed. (U. of Osaka, Sakai, Osaka)

Plenum Press NY 1990

0-30843478-4

TA1690.I53 1990 available in the NBS library series: Topics in Applied Chemistry, A. R. Katritzky and G. J. Sabong, eds.

As an example of phthalocyanine dyes, the following 60 entries are in the Aldrich Chemical Catalog:

TABLE 1

PHTALOCYANINE DYES (Aldrich Chemical Company)

| | |
|---|---|
| #412066 | Name: TETRAKIS(4-CUMYLPHENOXY)PHTHALOCYANINE, 97% |
| #404543 | Name: TIN(II) PHTHALOCYANINE |
| #406481 | Name: SILICON PHTHALOCYANINE DIHYDROXIDE Cata |
| #414387 | Name: VANADYL 2,9,16,23-TETRAPHENOXY-29H,31H-PHTHALOCYANINE |
| #393932 | Name: MANGANESE(III) PHTHALOCYANINE CHLORIDE |
| #410160 | Name: IRON(II) PHTHALOCYANINE BIS(PYRIDINE) COMPLEX |
| #404551 | Name: TITANYL PHTHALOCYANINE |
| #418145 | Name: 1,8,15,22-TETRAPHENOXY-29H,31H-PHTHALOCYANINE |
| #418153 | Name: 2,9,16,23-TETRAPHENOXY-29H,31H-PHTHALOCYANINE |
| #379573 | Name: IRON(III) PHTHALOCYANINE CHLORIDE Catal |
| #406473 | Name: TIN(IV) PHTHALOCYANINE DICHLORIDE Catal |
| #415448 | Name: NICKEL(II) TETRAKIS(4-CUMYLPHENOXY)PHTHALOCYANINE |
| #418161 | Name: 1,8,15,22-TETRAKIS(PHENYLTHIO)-29H,31H-PHTHALOCYANINE |
| #418188 | Name: 2,9,16,23-TETRAKIS(PHENYLTHIO)-29H,31H-PHTHALOCYANINE |
| #408808 | Name: GALLIUM(III) PHTHALOCYANINE CHLORIDE Ca |
| #418986 | Name: ALUMINUM 2,9,16,23-TETRAPHENOXY-29H,31H-PHTHALOCYANIN |
| #310204 | Name: COPPER(II) 4,4',4",4'''-TETRAAZA-29H,31H-PHTHALOCYAN |
| #402737 | Name: MAGNESIUM PHTHALOCYANINE |
| #402745 | Name: DISODIUM PHTHALOCYANINE |
| #418250 | Name: ALUMINUM 2,9,1 |
| #341169 | Name: ZINC PHTHALOCYANINE |
| #379557 | Name: MANGANESE(II) PHTHALOCYANINE Catalog Nu |
| #414379 | Name: NICKEL(II) 2,9,16,23-TETRAPHENOXY-29H,31H-PHTHALOCYAN |
| #433462 | Name: METHYLSILICON( |
| #418234 | Name: ZINC 2,9,16,23-TETRAKIS(PHENYLTHIO)-29H,31H-PHTHALOCY |
| #418242 | Name: ALUMINUM 1,8,1 |
| #379549 | Name: IRON(II) PHTHALOCYANINE |
| #408875 | Name: LEAD(II) TETRAKIS(4-CUMYLPHENOXY)PHTHALOCYANINE |
| #393894 | Name: VANADYL 3,10,17,24-TETRA-TERT-BUTYL-1,8,15,22-TETRAKI |
| #432946 | Name: COPPER(II) TET |
| #441082 | Name: GALLIUM(III) P |
| #423157 | Name: 2,9,16,23-TETR |
| #393886 | Name: COPPER(II) 3,10,17,24-TETRA-TERT-BUTYL-1,8,15,22-TETR |
| #418269 | Name: ALUMINUM 1,8,1 |
| #423165 | Name: COPPER(II) 2,9 |
| #430994 | Name: ZINC 2,9,16,23 |
| #307696 | Name: COBALT(II) PHTHALOCYANINE Catalog Number |
| #432180 | Name: SILICON 2,9,16 |
| #446637 | Name: ALUMINUM PHTHA |
| #253103 | Name: 29H,31H-PHTHALOCYANINE, 98% Catalog Num |
| #379565 | Name: LEAD(II) PHTHALOCYANINE |
| #418277 | Name: ALUMINUM 2,9,1 |
| #362530 | Name: ALUMINUM PHTHALOCYANINE CHLORIDE Catalo |
| #444529 | Name: ZINC 1,2,3,4,8 |
| #452521 | Name: IRON(III) PHTH |
| #446645 | Name: COBALT(II) 1,2 |
| #446653 | Name: COPPER(II) 1,2 |
| #448044 | Name: IRON(II) 1,2,3 |

TABLE 1-continued

| PHTALOCYANINE DYES (Aldrich Chemical Company) | |
|---|---|
| #386626 | Name: ALUMINUM 1,4,8,11,15,18,22,25-OCTABUTOXY-29H,31H-PHTH |
| #360635 | Name: NICKEL(II) PHTHALOCYANINE Catalog Number |
| #448311 | Name: COPPER(II) 1,2 |
| #428159 | Name: SILICON(IV) PH |
| #386618 | Name: COPPER(II) 1,4,8,11,15,18,22,25-OCTABUTOXY-29H,31H-PH |
| #287768 | Name: SILICON PHTHALOCYANINE DICHLORIDE Catal |
| #408883 | Name: NICKEL(II) 1,4,8,11,15,18,22,25-OCTABUTOXY-29H,31H-PH |
| #383813 | Name: ZINC 1,4,8,11,15,18,22,25-OCTABUTOXY-29H,31H-PHTHALOC |
| #362549 | Name: DILITHIUM PHTHALOCYANINE |
| #383805 | Name: 1,4,8,11,15,18,22,25-OCTABUTOXY-29H,31H-PHTHALOCYANIN |
| #252980 | Name: COPPER(II) PHTHALOCYANINE Catalog Number |
| #245356 | Name: COPPER(II) PHT |

An example of a traditional near-IR absorbing dye, also used for diagnostic purposes, is Aldrich #22886-9 dye, indocyanine green. Another, used as a biological stain, is Aldrich #11991-1, naphthol green B. Of all these dyes, a particularly good choice for this application are the naphthalocyanine dyes which have low water solubility but high solubility in non-polar polymers. For example, vanadyl 5, 14, 23, 32-tetraphenyl 2,3-naphthalocyanine [Aldrich 39,317-7 (CA 131220-68-3)] with a molecular formula weight of 1084 daltons exhibits a strong absorption peak (with a molar extinction coefficient of 200,000 at 846 nm) and high solubility in ethylene vinyl acetate (EVA) low melting polymers (such as Dupont ELVAX™ 410). This dye absorption peak matches well the emission wavelength of selected GaAlAs laser diodes. Similarly, vanadyl 2, 11, 20, 29-tetra-tert-butyl-2,3-naphthalocyanine [CA 105011-00-5] FW1004 absorbs near IR with a narrow peak at 808 nm which closely matches the emission wavelength (selected by choosing a different value of [Al]) of GaAlAs laser diodes widely used to pump solid state Nd:YAG lasers. All these naphthalocyanine dyes (Table 2) are highly soluble in EVA polymer thermoplastics and other similar thermoplastic materials. They are quite stable compounds particularly with heating to 300° C. and do not exhibit adverse photochemistry which might affect biological macromolecules in the tissue.

A table of naphthalocyanine dyes as presented in the Aldrich Catalog is presented below:

TABLE 2

| NAPHTHALOCYANINE DYES (Aldrich Chemical Company) |
|---|
| 1) vanadyl 5,14,23,32-tetraphenyl 2,3-naphthalocyanine<br>Aldrich 39,317-7CA 131220-68-3FW1084 846 nm p. 104 |
| 2) tin(IV) 2,3-naphthalocyanine dichloride<br>Aldrich 40,651-1CA 26857-61-4 FW902 828 nm p. 102 |
| 3) silicon (IV) 2,3-naphthalocyanine dihydroxide<br>Aldrich 40,653-8CA 92396-90-2 FW775 785 nm p. 94 |
| 4) silicon(IV) 2,3-naphthalocyanine dioctyloxide<br>Aldrich 40,767-4CA 92941-50-9 FW941 798 nm p. 94 |
| 5) 5,9,14,18,23,27,32,36-octabutoxy 2,3-naphthalocyanine<br>Aldrich 41,207-4CA 105528-25-4FW1292 867 nm p. 181 |
| 6) copper(II) 5,91,14,18,23,27,32,36-octabutoxy 2,3-naphthalocyanine<br>Aldrich 41,528-6CA 155773-67-4FW 853 nm p. 33 |
| 7) nickel(II) 5,9,14,18,23,27,32,36-octabutoxy-2,3-naphthalocyanine<br>Aldrich 41,885-4CA 155773-70-9FW1348 848 nm p. 78 |

TABLE 2-continued

| NAPHTHALOCYANINE DYES (Aldrich Chemical Company) |
|---|
| 8) vanadyl 2,11,20,29-tetra-tert-butyl-2,3-naphthalocyanine<br>Aldrich 43,296-2CA 105011-00-5FW1004 808 nm p. 1524 '96 |

A variety of wavelengths of electromagnetic energy can be used in the practice of the invention provided that suitable materials are used. In particular, it is important that the transfer film 54 absorb sufficient energy (or contains one or more dyes that absorb sufficient energy) at the chosen wavelength to melt or nearly melt the thermoplastic polymer in the targeted region. For thermoplastic materials such as ethylene vinyl acetate (EVA), a wavelength of about 3 to about 10 micrometers is preferred as these materials intrinsically absorb in this range. In one embodiment, the power of the laser is used generally in the range of from about 1 mW to about 200 mW depending on the size of the target (i.e, increasing power with increasing target size). It is also preferred that the wavelengths for laser activation and film absorption be chosen outside the normal range used for microscopic imaging. Reproducible microtransfer of tissue can be obtained using a variety of infrared wavelengths from the laser.

Suitable lasers for use in the present invention include carbon dioxide lasers (9.6–11 $\mu$m wavelengths), laser diodes, tunable single frequency Ti:sapphire lasers and diode-pumped NdYAG lasers. The wavelength outputs from these lasers can preferably range from ultraviolet to infrared. A particularly desirable laser for use with the present invention is the laser diode with wavelengths between 690 and 1300 nm. In this wavelength range, conventional glass microscope optics is highly transmissive and can be used to focus the laser. Other materials such as clear plastic support layers (e.g., polyester) for the thermoplastic film or pressure plates made of glass or plastic are also highly transmissive (with very low absorption) and therefore can be used easily. This is a marked improvement over laser capture microdissection designs using longer laser wavelengths (e.g., 9.6–11 $\mu$m) for the carbon dioxide laser or 3 um with the Er:YAG with laser diode pumping or- intrinsic).

Figure 10A:
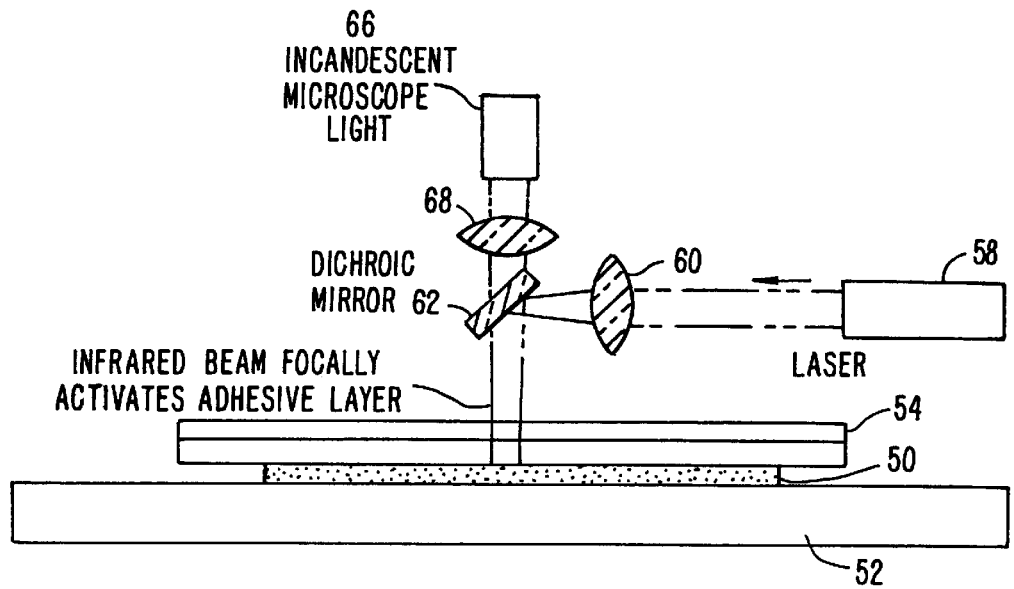
FIGS. 10a–10b schematically depict various embodiments of laser capture microdissection apparatuses.
Figure 10B:
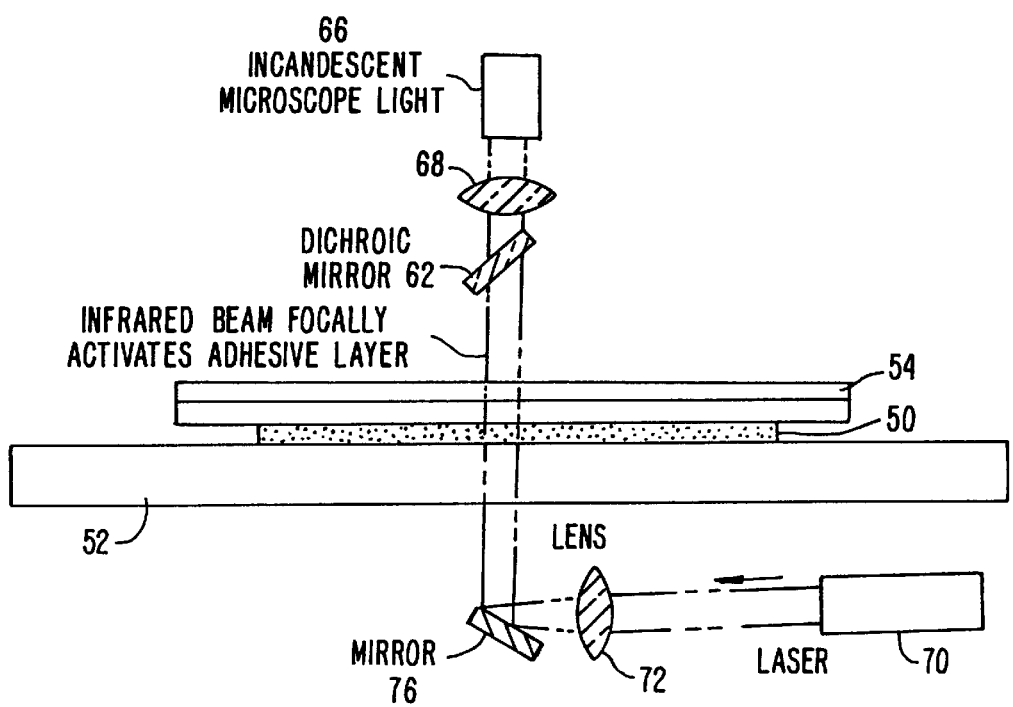

As shown in FIGS. 10A and 10B, the use of a compact laser diode 58 allows the laser 58 to be easily incorporated into a conventional microscope housing. For example, in FIG. 10A, incandescent light 66 from the microscope can be used, through a lens 68 and dichroic mirror 62, to identify and focus on the tissue which is desired to be extracted. Light from the laser diode 58 can then be focused through lens 60 and dichroic mirror 62 along the same effective optical path to allow ready dissection of the tissue which has been identified through the microscope. This "epi-irradiation" approach provides the advantages of using the same optics (microscope objective) to project high quality imaging of the specimen and also to focus the laser beam to small spots. The economy of using high quality microscope objectives for this dual function simplifies access to the sample 54. In general, higher imaging magnification will be coupled to smaller, higher precision laser capture microdissection targeting in this configuration.

By contrast, an advantage of the previously disclosed laser capture microdissection configuration shown in FIG. 9 is that imaging magnification and target spot size are decoupled and therefore more easily independently varied. In this later case, a targeting decision could easily be based on a high resolution image and then a simple adjustment of the laser spot made to match the target size. With the "epi-irradiation" design of FIG. 10A, such adjustments would be most easily accomplished by either multiple pulses or by switching (swivel) the microscope objectives after imaging to give appropriate spot size.

The configuration of FIG. 10B addresses the problem of effectively projecting the heat provided by laser 70. More specifically, in the configurations of FIGS. 9 and 10A, the laser first irradiates the top surface of a thermoplastic polymer film 54. In this case, the top of the film 54 absorbs a significant fraction of the laser pulse and is heated more rapidly than the lower surface. Consequently this top surface of the film 54 melts more rapidly. In this configuration, the intrinsic spot size is limited by the film thickness and thermal diffusional broadening of the heated spot of the film at the tissue specimen surface. By projecting the laser light through lens 72 and mirror 76 onto the bottom surface of the film 65, the laser capture microdissection can be performed on much smaller target spots (as small as 4 um) and with much shorter pulses (as short as 5 msec) to result in more precise targeting of small components (e.g., single cells or cell nuclei) and exposing them to briefer thermal transients. The later is important in quantitative recovery of molecular function, particularly enzymatic activity within the targeted cells, which is important in subsequent molecular analysis that is performed with tissue procured by the laser capture microdissection.

Indicators may also be included, either in the selectively adhesive transfer film or in a separate layer or layers, to define the location of the optical activation. Such indicators include thermochromic dyes, dye precursors which combine upon melting to form a color for visible or instrumental identification, and dyes which are converted to color by other effects of optical absorption. Suitable indicators also include other physical effects, such as the appearance or disappearance of translucency or opacity upon optical exposure or upon heating.

While wishing not to be bound by theory, it is thought that when such thermoplastic films are heated to near or at the melting point they flow and conform to an adjacent surface (in this case, the targeted tissue sample), forming a strong surface bond. This bond is thought to occur without actual chemical cross-linking to the tissue sample. Such strong bonds are formed most reliably when pressure is applied to force the flow of the "melt" into tight conformity with the sample surfaces. However, by using smooth films applied in close apposition to the tissue and delivering appropriate pulse parameters to selected composition thermoplastic films, one can reliability heat the film to peak temperatures associated with high film fluidity for a sufficient period of time to form adequately strong bonds between the film and tissue for highly reproducible focal microtransfer to occur. Moreover, by using a pulsed infrared laser source to activate the focal bond of the targeted tissue to the film, the targeted tissue is quantitatively procured (virtually complete microtransfer to the film) without chemical modification, while preserving focal tissue morphology and allowing unaltered microscopic observation prior to, during, and following the microtransfer.

An optional additional step may also be used in laser capture microdissection to improve the bonding between the cells of interest and the activated polymer film and decrease the bonding of the tissue of interest to the substrate. For example, the slide can be chosen to be a material that has an inherently lower affinity for the tissue sample than the polymer film has for the tissue sample. Alternatively, the slide can be pretreated with a monolayer of silicone oil or 3% aqueous glycerol solution to reduce the adhesion of the tissue subsequently placed on the slide and increase the ease with which the activated film removes the tissue. In another variant, this tissue or film can be coated with a "release agent" such as silicone oil or a directly bonded silicone polymer. In this way, the film will exhibit no affinity for the tissue in regions which are in contact with the tissue but not thermally (laser) activated. Thermal activation will cause focal melting of the bulk film polymer and thus disrupt and dilute the surface monolayer of release agent in the region to be bonded. Therefore, the targeted tissue bond strength is unaffected by the release agent. In a fourth example, an adhesive layer such as poly-L-lysine can be coated onto the slide before application of the tissue section. This adhesion strengthens the attachment of the tissue to the slide, thereby reducing non-specific transfer when the film is pressed onto the tissue before laser activation. Although many such treatments may make specific transfer more difficult (i.e., requiring greater bond strength of the film with the underlying tissue), an adhesive coating such as poly-L-lysine that has a high affinity for and forms a strong bond with the melted thermoplastic film may inhibit non-specific transfer while facilitating complete specific transfer of the targeted regions. Finally, in a fifth example, the tissue can be enclosed in a polymeric material which will form a strong bond with the meltable film and be sufficiently water-soluble to allow the tissue sample to be retrieved in the analysis step. The enclosure of the tissue in such a material can be done by a coating technique such as application of the polymer in solution or placing the material in film form on the tissue and melting it. It could also be in the form of a coating on the hot-melt film to enhance the bond of the meltable film to the tissue and decrease the bond to the slide.

The laser microdissection system can be advantageously used with a variety of sample preparations, such as stained thin sections of tissue or stained cytology specimens of intact cells. In this case, the transferred regions can be clearly identified in a microscope by the focally transferred stained material on an otherwise transparent film. Alternatively, the film and tissue slide can be indexed to an x-y coordinate system to give a specific slide location to each transferred point which may then be automatically recorded.

The microtransferred tissue may then be collected from the film, for example, by punching the precisely recorded spots directly into the desired reaction or extraction vessels (e.g., by automatic x-y translation) or by placing the whole film into a reaction vessel.

The molecular analysis of the extracted cellular material, for example by RT-PCR, in one embodiment of the invention requires localizing the small objects (e.g., 50 μm spots of tissue) adhering to the substrate and collecting them into an analysis chamber, for example, punched out into a vial. Using an x-y encoding of the position of each target site and automated translating allows the punching of area(s) to also be automated using the same coordinates, so long as the support film is not deformed or stretched in the application, activation and removal steps of the process. Thus, the sample collecting process is also amenable to automation. Alternatively, one can ensure that the target sites are at known positions on the transfer substrate. For example, multiple small pieces of adhesive transfer film can be selectively applied to those locations on the tissue which correspond to sites to be extracted, rather than applying a single large piece of substrate film to the entire specimen. Exemplary of such a scheme is small disks of adhesive film are applied at a fixed repeat distance on a continuous polyester film, preferably a strong and not easily stretched sheet, to provide a linear array of separately activatable target sites. After each target zone is identified, the next unused small adhesive spot in the linear array is locally applied at a fixed separation to this region by a small pressure plate or an air jet. The substrate/tissue slide as a unit is then micropositioned under microscope viewing to target specific cells (determined by the laser spot diameter) within the target zone (i.e., the diameter of the adhesive spots which is greater than the laser spot diameter). Where the substrate film and the mechanism applying these small pieces of film is located with respect to a stationary reference (e.g., the microscope objective) then it can be arranged that the adherent tissue spots will always be at known locations on the substrate film (e.g., in the center of a narrow strip of adhesive film at equally spaced distances). Targeting of like cells within the target zone is accomplished by microtranslating the sample between-sequential laser pulses. Thus, the operator positions the slide in the microscope so that the tissue of predetermined interest is at the center of the field, a pressure plate or other means can then adhere the adhesive film spot to the tissue such that the predetermined cells/objects of interest are within the known location on the support film. The adhesive is activated, for example, by the IR laser pulses, and the pressure plate is then released. The film is then separated from the specimen slide and advanced so that a fresh portion of film can be used at the next specimen location. The process allows all transfers to occur on an ordered series (numbered array) of spots with a fixed spatial separation, as the film is not distorted in the process. The size of the adhesive film spot determines the size of the target zone within which selection of the objects/cells are made for that one transfer (array number) in this embodiment of the invention. The target zone size is determined by the selection of the particular film (i.e., the geometry of ordered arrays), but can be increased or decreased, for example with parallel rows of spots of different sizes on the same support film.

In another embodiment of the invention that is further simplified, the collection process is performed by cutting off (rather than punching out) the desired portions of adhesive films. This simplified embodiment eliminates the requirement for close tolerances between a punch and die. Alternatively, other means can be used to separate the tissue/adhesive film from the rest of the tape. Such means to include direct peeling of the tape, focally dissolving either the adhesive tape or its bond to a substrate film, excising the spots with a hot wire knife (which is self-sterilizing to eliminate contamination between specimens).

An additional feature of the invention is directed to the identification of the samples. The small portions of film can have minute identifying marks (e.g., bar codes) attached to them which would be seen under the microscope and can be recorded along with a video image of the specimen. A practical way in which this is accomplished is to place the identifying marks on a mechanically strong substrate adjacent to each discrete spot of adhesive on the tape configuration mentioned above. An additional use of these identification marks is to control the advance of the tape for each new specimen. A sensor in the microscope or analysis of the various specimens determines when the mark is in, for example, the center of the field as the tape is being advanced. Alternatively, a mechanical drive (e. g., with sprockets) can be used to advance the tape a fixed known amount.

As a preferred embodiment of the invention, equally spaced adhesive film spots along with minute adjacent bar code identifiers are centrally placed on a thin (e.g. 1 mm wide), mechanically strong backing tape, for example, about 0.002 inch thick mylar, which is preferably supplied in a sterile cassette having a leader. The cassette and a stepper motor takeup drive are attached to the housing of an inverted microscope (or its stationary stage if the slide is to be moved by hand), so that the center of the tape is aligned with the center of the microscope objective (and field) and the tape is above the level of the specimen. The leader is attached to a spool on the drive shaft of a stepper motor and wound up enough so that the tape is firmly attached to the takeup motor and the first adhesive spot is nominally in position. A solenoid actuated pressure plate pushes down on the tape so that it is close enough to the specimen that a sensor in the microscope (video signal) can see the identifier marks before the tape is firmly attached to the specimen. The tape is then advanced to its final position and the pressure place is pushed firmly against the film. An IR laser is activated to bond the selected tissue to the adhesive film and shortly afterwards the pressure plate is released. The pressure plate solenoid, which also holds a fixture with two prongs which lie between the film and the stage is then temporarily actuated in the upwards direction so that the two prongs pull the tape off of the tissue. A next specimen is optionally selected by the operator and the pressure plate is activated in its partial down position so that the sensor can detect the identification mark and the process is repeated as desired. After the final specimen has been transferred, the motor advances the tape further and then the takeup spool and the cassette are removed and attached to the motor shafts of a collection mechanism mounted on the stage. This mechanism uses a hot wired knife to cut the adhesive spot/adherent tissue away from the rest of the tape and employs an air jet to separate the two (if necessary) and deposit the sample into either a vial or a 96 well microtitre plate. The known location of the adhesive spots along the length on the tape can be uses to properly position the first spot and advance the tape to subsequent positions. A computer-generated bar code correlated with the film label is attached to the vial or microtitre place for traceability. The bar code is stored in a computer data entry of the microtransfer sample (e.g., images, patient number, specimen number, etc.) as well as being recorded directly in the image of the target immediately after laser activation.

Laser capture microdissection (LCM) has many advantages over the prior art techniques. As an example of the benefits of the present invention, an individual glomerulus can be procured from a kidney tissue section sample in under ten seconds, and hundreds of glomeruli can be isolated by a single operator in one hour with minimal effort. One skilled in the art appreciates that such speed and efficiency cannot by approached by conventional microdissection methods.

It should also be appreciated that laser capture microdissection is not limited to use on biological samples. Indeed, the techniques described herein may be used for the sorting/removal of any object that need be discriminated from other objects in a microscopic field. For example, micromachined objects can be readily, rapidly and efficiently sorted under the practice of the invention. It should further be appreciated that the practice of the invention is not strictly limited to the use of electromagnetic energy as any energy source that provides for a specific, localized melting of the thermoplastic transfer film will operate in the invention. A heat source, for example, from an electrical circuit may be desirable when the region to be transferred is sufficiently large as in, for example, a relatively homogeneous tissue sample on the order of 1 millimeter in size. Also useful as sources of selective energy are electrically heated radiant heaters, irons or pencil heating probes, flashbulb generated energy (when used, for example, in conjunction with one or more precision masks, focused xenon lamps, as obtainable from ILC Technology, Inc. of Sunnyvale, Calif., and the like, as will be apparent to those skilled in the art based upon the disclosure herein.

Features and characteristics of the present invention will be illustrated by the following examples to which the present invention is not to be considered limited. In the examples and throughout, percentages are by weight unless otherwise indicated.

The following examples were performed in an attempt to establish if the present invention could be used to more specifically study protease distribution during human tumor invasion. Levels of MMP-2 and cathepsin B in fields of invasion breast and colon carcinoma were measured to assess if the enzymes in these regions were quantitatively increased as compared to matched numbers of normal cells from the same patient.

In the following examples, normal and tumor samples of colon and breast tissue from surgical resections were maintained in a frozen condition (−70° C.) until analysis. Tissue section of invasive breast and colon carcinoma were selected based upon histologic evaluation. The tumor sections of tissue which contained invasive tumor and stroma were preferentially selected instead of normal epithelium or significant numbers of inflammatory cells. The control sections of normal tissue contained epithelium and a thin section of underlying stroma. The proportion of epithelial and stromal tissue was similar for both normal and tumor sections.

In the examples, microdissection slides were prepared by covering standard histology slides with 200 microliters of warm agarose (1%) and overlaying a cover slip. After five minutes the coverslip was removed leaving a thin bed of agarose on the slide. Twenty micron thick frozen sections were prepared in a cryostat and placed on the agarose gel. The tissue was briefly dipped in eosin. Optimum microdissection was achieved by starting at the edge of each section and systematically dissecting and separating histologic fields of interest with the microdissecting device of FIG. 3. Areas of interest were retained on the slide for subsequent analysis. The DNA content of the specimens was determined by spectrophotometric measurement at 260 nm. The DNA content of each sample was proportional to the number of cells counted in each histologic section.

cDNA (and DNA) libraries of microdissected tissue sections are also provided for by the present invention as well as methods of making such libraries. Such libraries are useful, inter alia, in facilitating the identification of transcripts specifically expressed in cells of distinct histological origin and tumorigenic stage.

EXAMPLE 1

In this example, samples of normal and tumor tissue matched for cell number were analyzed from each subject. Levels of MMP-2 were determined by zymography and quantified using an Arcus scanner. Results were statistically analyzed using the students t-test. Cathepsin B levels were determined as $V_{max}$, against the substrate Z-Arg-Arg-NHMec.

The results of this example are set forth in Table 1 below which lists the cathepsin B activity in matched pairs of invasive colon carcinoma/normal epithelium, and invasive breast carcinoma/normal epithelium. Activity measurement are expressed as $V_{max}$, nmol/min×mg DNA. Cathepsin B activity was increased an average of 2.3 fold in the colon tumors (p<0.005), and 6.9 fold in the breast tumors (p=0.077).

TABLE 1

| SAMPLE | NORMAL | TUMOR | TUMOR/NORMAL |
|---|---|---|---|
| CATHEPSIN B ACTIVITY IN INVASIVE HUMAN COLON CARCINOMA | | | |
| 1 | 1.38 | 4.75 | 3.4 |
| 2 | 1.89 | 2.25 | 1.2 |
| 3 | 1.98 | 6.32 | 3.2 |
| 4 | 0.49 | 1.88 | 3.8 |
| 5 | 0.44 | 0.72 | 1.6 |
| 6 | 1.03 | 1.92 | 1.9 |
| 7 | 0.47 | 1.35 | 2.9 |
| 8 | 0.19 | 0.33 | 1.7 |
| 9 | 1.07 | 0.90 | 0.8 |
| 10 | 0.33 | 0.88 | 2.7 |
| Average | 0.93 | 2.13 | 2.3 |
| CATHEPSIN B ACTIVITY IN INVASIVE HUMAN BREAST CARCINOMA | | | |
| 1 | 0.63 | 3.02 | 4.8 |
| 2 | 0.51 | 10.08 | 19.8 |
| 3 | 0.61 | 4.43 | 7.3 |
| 4 | 2.21 | 2.38 | 1.1 |
| 5 | 2.06 | 3.72 | 1.8 |
| Average | 1.20 | 4.73 | 6.9 |

As can be seen from Table 1, all five breast tumors and nine of the ten colon tumors showed increased activity of cathepsin B as compared to matched numbers of normal cells from the same patient (Table 1). Increased activity in the colon tumors ranged from 19% to 283%, with an average increase in tumors of greater than two fold. The increase of cathepsin 2 activity was more pronounced in breast tumors with an average increase of slightly less than seven fold.

EXAMPLE 2

In this example, polymerase chain reaction (PCR) analysis was performed. On the basis of previously reported cDNA sequences of 72 kDa type IV collagenase, sense and antisense oligonucleotide primers were synthesized for amplification of the enzyme activation site (M. Onisto et al, "Reverse Transcription-Polymerase Chain Reaction Phenotyping of Metalloproteinases and Inhibitors in Tumor Matrix Invasion", Diagn. Mol. Pathol, 2(2):74–80, 1993). The paired oligonucleotide sequences were: 5'-CAA TAC CTG AAC ACC TTC TA (SEQ ID NO: 1), 3'-CTG TAT GTG ATC TGG TTC TTG (SEQ ID NO 2). Labeled PCR for Single Strand Conformation Polymorphism (SSCP) was obtained by combining the following in a 10 microliter reaction: 1 microliter 10× PCR buffer (100 mM Tris-HCL, pH 8.3; 500 mM KCl; 15 mM $MgCl_2$; 0.1% w/v gelatin); 1 microliter of DNA extraction buffer; 50 pmol of each primer; 20 nmol each of dCTP, dGTP, dTTT, and dATP; 0.2 microliter [$^{32}P$] dCTP (6000 Ci/mmol); and 0.1 unit Taq DNA polymerase. The amplification reaction was carried out for 30 cycles at 95° C. for 30 s, 60° C. for 30 s, and 72° C. for 30 s.

Figure 6A:
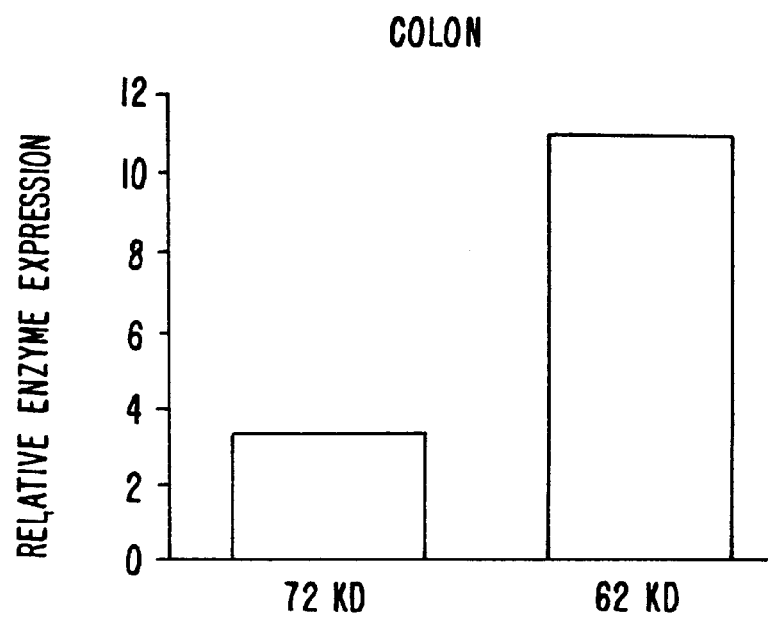
FIGS. 6a and 6b show the expression of MMP-2 in ten invasive colon carcinoma cases (FIG. 6a) and in five cases of invasive breast carcinoma (FIG. 6b) as compared to normal colonic mucosa from the same patients.

FIG. 6a shows the expression of MMP-2 in ten invasive colon carcinoma cases as compared to normal colonic mucosa from the same patients. The bar graphs show increases of approximately three fold in the 72 kDa pro-form of the enzyme (p<0.001) and ten fold in the 62 kDa active form of the enzyme (p<0.001).

Figure 6B:

FIG. 6b shows the expression of MMP-2 in five cases of invasive breast carcinoma. The bar graphs show an appropriate increase of three fold in the 72 kDa pro-form of the enzyme (p<0.05) and ten fold in the 62 kDa active form of the enzyme (p<0.05).

The 72 kDa pro-type IV collagenase and 62 kDa active form of the enzyme were increased in all ten colon tumors and all five breast tumors as compared to normal tissue from the same patient. The increase was greater in the 62 kDa active form of the enzyme which was elevated an average of ten-fold in both the colon and breast tumors as compared to normal control tissue. The 72 kDa pro-enzyme levels were increased an average of three fold in both tumor types. For both breast and colon tumors the increase in the 62 kDa active enzyme was more variable than that of the pro-enzyme. Elevations in the 62 kDa active enzyme in tumors ranged from 3 to 20 fold while increases in the 72 kDa pro-enzyme were consistently in the 2 to 5 fold range. These results are similar to the recent findings of Davis et al ("Activity of Type IV Collagenases in Benign and Malignant Breast Disease", Br. J. Cancer, 67:1126–1131, 1993) in their analysis of human breast tumors. These authors performed zymogram analysis of tissue sections from human breast cancer patients. These analyses demonstrated that the fraction of total MMP-2 present as the 62 kDa activated form was statistically elevated in malignant disease, and a high proportion of this active enzyme species was detected in higher grade tumors. The present invention extends this analysis by comparing and quantitating both 72 kDa and 62 kDa forms of the enzyme in specific regions of invasive tumor and matched normal control epithelium from the same patient.

EXAMPLE 3

In this example, strand conformation polymorphism (SSCP) analysis was preformed. Labeled amplified DNA was mixed with an equal volume of formamide loading dye (95% formamide; 20 mM EDTA; 0.05% bromophenol blue, and 0.05% xylene cyanol). The samples were denatured for 5 min at 95° C. and loaded onto a gel consisting of 6% acrylamide (49:1 acrylamide:bis), 5% glycerol, and 0.6× TBE. Samples were electrophoresed at 8 W at room temperature overnight. Gels were transferred to 3 mm Whatman paper, dried and autoradiography was performed with Kodak X-OMAT film.

Figure 7:
FIG. 7 shows SSCP analysis of MMP-2 activation site.
Figure 7:

FIG. 7 shows SSCP analysis of MMP-2 activation site. The figure shows representative cases of normal colon is mucosa compared to invasive colon carcinoma, and normal breast tissue compared to invasive breast carcinoma. No difference is observed between the normal and tumor specimens. The two band in each lane represent single and double forms of DNA. Similar results were obtained for ten colon carcinomas and four breast carcinomas.

To assess if increased tumor levels of activated MMP-2 are due to a mutation in the enzyme, PCR was used to amplify DNA sequence coding for the activation site of gelatinase A from the colon and breast tumors. The activation site is located 10 kDa from the N-terminus of the enzyme and contains the site of cleavage which converts the 72 kDa pro-enzyme into the 62 kDa active species. Amplification and analysis of this region by PCR and SSCP showed no detectable mutations in any of the ten colon tumors or four breast tumors studied. These results suggest that increased levels of active enzyme in invasive tumors is most likely due to a tumor associated activating species. The sensitivity of PCR amplification of DNA from microdissected frozen tissue sections was determined to be less that one high power field. Similar to the amplification of DNA, amplification of mRNA from small cell populations was preformed according to the present invention using reverse PCR.

A previous study indicated that MMP-2 is up-regulated in human colon carcinoma. However, recently several studies using in situ hybridization analysis report that the MRNA level of MMP-2 in human colon carcinoma is increased in the stromal cells as opposed to the tumor cells. In order to address this possibility frozen tissue sections were microdissected to measure enzyme levels of MMP-2 in separate tumor and stromal cell populations. From a single high power field sufficient tissue was recovered to quantitate enzyme levels by zymography. Studies of invasive tumor cells and adjacent stroma from three cases indicate that 72 kDa pro-MMP-2 and active 62 kDa form are associated with both tumor cell and stromal cell populations. Preliminary data suggest that the highest enzyme levels are at the tumor-stroma interface.

EXAMPLE 4

Human prostate cancer has been proposed to progress through an in situ tumor phase called prostatic intraepithelial neoplasia (PIN) prior to evolving into overtly invasive cancer. PIN lesions are frequently found in association with prostate carcinoma, and histologically the cells in PIN foci have several features similar to those of invasive prostate cancer cells. Previous reports have shown that PIN lesions are frequently aneuploid. However the precise relationship between PIN and invasive carcinoma has remained unclear.

In this Example, frozen normal and tumor prostate samples from 100 patients treated with transurethral prostatectomy or radial prostatomy were collected. Of these, 30 cases which contained clearly invasive cancer as well as at least one focus of identifiable PIN were selected for study during this Example. Fourteen of the set cases contained more than one focus of PIN. The histopathology of the tumors was variable and included well-differentiated, moderately differentiated and poorly differentiated. PIN lesions were both low and high grade.

Microdissection of selected populations of normal epithelial cells, cells from PIN lesions, and invasive tumor cells from frozen tissue sections was performed under direct light microscopic visualization utilizing the method discussed above and shown in FIGS. 8a–8d. Specific cells of interest were microdissected and procured from unstained 8 μm frozen sections. In each case, normal epithelium, PIN cells, and invasive tumor cells from the same patient were analyzed.

5–10 micron sections of formalin-fixed, paraffin-embedded tissue or frozen tissue were prepared on a glass slide according to conventional surgical pathology Protocol.

The paraffin sections were deparaffinized with xylene (×2), 95 ethanol (×2), 50% ethanol (×2), distilled water (×2), and air dried. Frozen or paraffin sections were stained briefly in eosin (1% eosin in 80% ethanol) and air dried.

An adjacent hematoxylin and eosin section was used to assess the tissue section for optimal areas of microdissection, i.e., localization of specific small cell populations of interest, exclusion of regions which contain significant inflammation, etc.

Microdissection of selected populations of cells was performed under direct light microscope visualization. A sterile 30-gauge needle was used as the transfer surface. Electrostatic interaction between the needle and cellular material provided the adherence needed to remove selected populations of cells. It was determined that pure cell populations of as little as 5 cells could be procured. In addition it was found possible to procure cells arranged as a single cell layer, i.e., normal epithelium, epithelial lining of cystic lesions, etc.

Procured cells were immediately resuspended in a 20 ml solution containing 10 mM Tris-HCL, pH 8.0, 100 µm ethylenediamine tetraacetic acid (EDTA), 1% Tween 20, 0.1 mg/ml proteinase K, and incubated overnight at 37° C. The mixture was boiled for 5 minutes to inactivate the proteinase K and 0.5–2% of this solution was used for polymerase chain reaction (PCR) analysis.

The oligonucleotide primers D8S136, D8S137, and NEFL were used to locate chromosome 8p12–21. Reactions with D8S137 and NEFL were performed in an MJ Research thermal cycler as follows: 2 minutes at 950° C., followed by 40 cycles of: 950° C. for 30 seconds, 620° C. for 30 seconds, 720° C. for 30 seconds, followed by a final 2 minute incubation at 720° C.

Reactions with D8S136 were cycled as follows: 2 minutes at 950° C., followed by 40 cycles of: 950° C. for 30 seconds, 550° C. for 30 seconds, 720° C. for 30 seconds, followed by a final 2 minute incubation at 720° C.

PCR was performed in 12.5 ml reactions with 200 mM dNTP, 0.8 mM primers, 2 µl of alpha [$^{32}$P] dCTP (NEN), and 1 unit of Taq polymerase. Labeled amplified DNA was fixed with an equal volume of formamide loading dye (95% formamide; 20 mM EDTA; 0.05% bromophenol blue, and 0.05 xylene cyanol).

The samples were denatured for 5 min at 950° C. and loaded into a gel consisting of 7% acrylamide (49:1 acrylamide:bis), 5.7 M urea, 32% formamide, and 0.089 M Tris, 0.089 M borate. 0.002 M EDTA (1× TBE). Samples were electrophoresed at 95 Watts for 2–4 hours. Gels were transferred to 3 mM Whatman paper, and autoradiography was performed with Kodak X-OMAT film. The criterion for loss of heterozygosity (LOH) was complete, or near complete absence of one allele as determined by visualization. Cases with LOH showed two alleles in the normal epithelium control and one allele in the tumor or PIN all with similar intensities. Cases with complete or near complete loss (i.e., very faint band) of one allele in tumor or PIN were considered positive for LOH at that marker.

The present inventive method was used to microdissect cells from tissue sections to study loss of heterozygosity on chromosome 8p12–21 in patients with both prostatic carcinoma and adjacent foci of PIN. Tissue microdissection was conducted on 30 patients with concomitant PIN and invasive prostate cancer. In each case normal epithelium, invasive prostate cancer and at least one focus of PIN from the same patient were examined. In 14 cases multiple foci of PIN were examined. In all cases each individual PIN lesion and corresponding invasive tumor were selectively microdissected from adjacent stroma, normal epithelium and inflammatory cells. Essentially pure populations of cells of interest were procured.

LOH on chromosome 8p12–21 occurred in at least one PIN lesion in 26 of 29 (89.6%) informative cases. Fourteen of the cases contained more than one PIN lesion. Eleven of these cases showed different allele loss patterns among the PIN lesions, including lose of opposite alleles. In total, 8p12–21 LOH was seen in 63.6% (35/55) of PIN lesions studied. Allelic loss of chromosome 8p12–21 was seen in invasive tumors in 28 of 29 (96.5%) patients. In contrast with the success associated with the adhesive transfer technique of the present invention, the use of a scraping dissection technique produced an LOH of less than 15%. This indicates the sensitivity of the adhesive transfer of the present invention is much greater than conventional techniques.

EXAMPLE 5

Nascent in situ breast carcinomas are frequently observed arising in association with a spectrum of epithelial hyperplasia and invasive carcinoma. Pathologists have historically interpreted the common association of atypical hyperplasia, in situ carcinoma and invasive carcinomas as evidence for a relationship among the entities.

The polymorphic DNA marker used in this Example was PYGM located on chromosome 11q13. Reactions were cycled in a thermal cycler as follows: 94° C. for 1.5 min., 55° C. for 1 min., 72° C. for 1 min. for a total of 35 cycles. PCR was performed in 10 µl volumes and contained 1 µl 10× PCR buffer (100 mM Tris-Hcl, pH 8.3; 500 mM KCl; 15 mM MgCl$_2$; 0.1% w/v gelatin; 2 µl of DNA extraction buffer, 50 pM of each primer; 20 nM each of dCTP, dGTP, dTTP, and dATP; 0.2 µl [$^{32}$P] dCTP (6000 Cl/mM); and 0.1 unit Taq DNA polymerase. Labeled amplified DNA was mixed with an equal volume of formamide loading dye (95% formamide; 20 mM EDTA; 0.05% bromophenol blue; and 0.05% xylene cyanol). The samples were denatured for 5 min. at 95° C. and loaded into a gel consisting of 6% acrylamide (49:1 acrylamide:bis). Samples were electrophoresed at 1800 volts for 2–4 hours. Gels were transferred to 3 mM Whatman paper, dried and autoradiography was performed with Kodak X-OMAT film. The criterion for LOH from the microdissected in situ and invasive breast samples was complete absence of an allele.

Using the adhesive transfer technique of the present invention, cells were microdissected from normal epithelium, in situ carcinoma and invasive carcinoma from 8 µm thick formalin fixed deparaffinized sections from individual biopsies. Allelic loss of chromosome 11q13 was found in 69% of human breast carcinoma cases studied (n=105). The allelic loss was observed in both the in situ and invasive components of the tumors. In all cases (26/28) where in situ and invasive cancer was present in the same section, the identical allele was lost in the in situ and the invasive carcinoma. This provides molecular support for the long-held hypothesis that in situ breast cancer is a precursor to invasive cancer.

In order to finely map the LOH locus on chromosome 11q13, Genome Center provided a series of SSCP probes mapped to the relevant region of chromosome 11. The initial LOH area was determined to be bracketed by the proximal marker PYGM, and by the distal marker INT-2. A subset of 20 of the 105 cases exhibited LOH of either INT-2 or PYGM, but not both. Using these special cases, a series of intervening markers were used to map the smallest overlapping region between INT-2 and PYGM which shows LOH. It has been possible to pinpoint the LOH zone to a region encompassed by only one or two YAG or Cosmid clones at a location which overlaps with the MEN-1 (Multiple Endocrine Neoplasia type 1) locus.

Sequencing gel analysis was performed on PCR-amplified DNA isolated from human tissue microdissected by the method depicted in FIGS. 8a–8b. The results indicated that microdissection of frozen tissue sections allows for more specific analysis of cell populations within human tumors than conventional techniques. The microdissection technique of the present invention may be used in combination with a number of different technologies that allow for analysis of enzymes, mRNA and DNA from pure populations or subpopulations of particular cell types. This simple technique may have utility in characterizing protease distribution during human tumor invasion, precisely determining protease expression in tumor and/or stromal cell populations as an indicator of tumor aggressiveness, and monitoring the effectiveness of anti-protease therapeutic agents in inhibiting protease activity at the tumor-stromal interface. In addition, combination of this microdissection technique with PCR, RT-PCR, differential display and SSCP may identify genetic alterations in specific subpopulations of tumor or stromal cell that would not be evident in heterogeneous human tumor samples.

EXAMPLE 6

Standard 6 μm sections from formalin or alcohol-fixed, paraffin-embedded archival tissue samples were prepared on noncoated glass slides. Sections were deparaffinized, stained with hematoxylin and eosin, treated with 3% glycerol in water for 1 minute and air dried prior to Laser Capture Microdissection (LCM). Fresh tissue, when used, was snap frozen immediately after surgery at −70° C. 6 μm cryostat sections were prepared on standard glass on standard glass histology slides. Tissue sections were fixed in formalin or alcohol, and stained with hematoxylin and eosin (Lerner Laboratories, Pittsburgh, Pa.). Sections were dehydrated in graded alcohols and air-dried for 5 minutes prior to LCM transfer.

For LCM transfer, 100 μm thick, flat films were made by spreading a molten ethylene vinyl acetate EVA, (Adhesive Technologies, Hampton, N.J.) onto smooth siliconized or polytetrafluoroethylene surfaces. The optically transparent, thin films were placed on top of tissue sections, and the tissue/film sandwich was viewed in an inverted microscope (Olympus Model CK2, Tokyo) at 100× magnification (10× objective). A pulsed carbon dioxide laser beam was introduced via a small front-surface mirror coaxial with the condenser optical path so as to irradiate the upper surface of the EVA film. The carbon dioxide laser (either Apollo Company Model 580, Los Angeles, Calif. or California Laser Company Model LS150, San Marcos, Calif.) provided the individual pulses of adjustable pulse length and power. A ZnSe lens focused the laser beam to an adjustable spot size onto the target specimen. For 150 mm diameter transfer spots, 25 to 30 mW was delivered to the film during a 600 msec pulse. For smaller or larger spots, the power was decreased or increased approximately in proportion to the diameter of the laser spot focused on the target area. The absorption coefficient of the EVA film measured both by FT-IR spectrometry and direct transmission was about 200 cm$^{-1}$ at a laser wavelength of 10.6 μm. Since greater than 90% of the laser energy was absorbed within the thermoplastic film, little direct heating of the tissue specimen occurred. The glass slide provided a large heat sink which served to confine the full-thickness, transient, focally molten plastic with the targeted tissue. After cooling and recrystallization, the film formed a local surface bond to the targeted tissue stronger than the adhesion forces of the tissue to the slide. The film and targeted cells were removed from the tissue specimen, resulting in focal microtransfer of the targeted tissue to the film surface.

For polymerase chain reaction, the tissue film and adherent cells were immediately resuspended in 40 μl of a solution containing 10 mM Tris-HCl (pH 8.0), 1 mM EDTA, 1% Tween 20, and 0.1 mg/ml proteinase K, and incubated overnight at 37° C. The mixture was then boiled for 10 minutes to inactivate the proteinase K. The tubes were briefly spun (1000 rpm, 1 minute) to remove the film, and 0.5 μl of the supernatant was used for PCR. For the most efficient transfer recovery, the transfer film is initially applied to the tissue section as a circular disk of about 0.5 cm diameter. After LCM transfer the disk placed into a well in a 96 well microtitre plate containing 40 μl extraction buffer.

For polymorphic DNA studies, oligonucleotides for the loci D8S136 and D8S33 located on chromosome 8q, D17S855 located on chromosome 17q21, D11S449 located on chromosome 11q13, D9S171 on chromosome 9p, specific primers for exon 2 of the VHL gene, and specific primers for *Mycobacterium* tuberculosis were used (Research Genetics, Huntsville, Ala.). All PCR reactions included incorporation of $^{32}$P-DCTP for visualization of the PCR product, with the exception of the amplification of *M. tuberculosis* which was visualized by ethidium bromide staining.

For reverse transcription-polymerase chain reaction (RT-PCR), total RNA was extracted from the tissue sample after LCM using a modification of a published RNA microisolation protocol (Stratagene, La Jolla Calif.). Volumes were proportionally adjusted downwards, and a 10-fold increase in glycogen carrier (10 ng/ml) was used in all precipitation steps. After initial recovery and resuspension of the RNA pellet, a Dnase step was performed for 3 hours at 37° C. using 10 u/ml of Dnase (GenHunter, Nashville), in the presence of 4 units of Rnase inhibitor (Perkin Elmer), followed by re-extraction of the RNA. The integrity of the RNA sample may be determined by RT-PCR of, for example, actin mRNA using actin-specific primers (Clonetech, Palo Alto, Calif.). The resuspended RNA was reverse transcribed using 5 μM random hexamer primers (Perkin Elmer), 250 mM dNTPs and 100 units reverse transcriptase (MMLV, GenHunter, Nashville, Tenn.).

Reverse transcription was accomplished by heating the RT mix (without enzyme) to about 65° C. for 5 minutes, followed by primer annealing for 10 minutes at about 25° C. The reverse transcriptase was then added, followed by further incubation at 25° C. for 10 minutes, 37° C. for 40 minutes and 94° C. for 5 minutes. PCR was performed with specific actin or PSA primers, and the products subjected to denaturing electrophoresis gel analysis.

EXAMPLE 7 cDNA libraries were generated using material isolated by laser capture microdissection. Double stranded cDNA is prepared from approximately 5 µg of total cellular RNA based on the RNaseH-mediated second strand replacement method. The reverse transcription first strand synthesis was primed with about 50 ng/µl of oligo(dT). The reaction was carried out at about 45° C. for 15 minutes. The second strand replacement and addition of EcoRI linkers were performed as suggested by the manufacturer (Superscript Choice System, Life Technologies Inc., Gaithersburg, Md.). After second strand synthesis, the reaction product was electrophoresed and fragments from about 0.3 kb to about 2 kb were gel isolated from 1% low melting point agarose using beta-agarose (New England Biolabs, Beverly, Mass.). The cDNA pellet was resuspended in 20 µl Tris-EDTA and stored at −20° C.

Five microliters of the isolated cDNA was amplified by 5 cycles of PCR under standard conditions and the linker-specific primer LINK that also functions to direct UDG cloning. The cDNA was first denatured for 3 minutes at 95° C., followed five time by the following cycle: 15 seconds at 95° C.; 15 seconds at 55° C.; and 2 minutes at 72° C. A final extension was performed for 5 minutes at 72° C. The oligonucleotide primers, nucleotides, enzyme, etc. were removed from the reaction mix by column chromatography (CHROMA SPIN-200, Clontech, Palo Alto, Calif.). The column flow through was ethanol precipitated and resuspended in 20 µl of Tris-EDTA. Six microliters of the product was cloned into the UDG cloning vector pAMP10 according to the manufacturer's instructions (Life Technologies Inc., Gaithersburg, Md.). A complex and relatively low redundancy library of approximately 200,000 clones was prepared in this way.

cDNA libraries produced under the practice of the invention have many advantages not heretofore attainable, such as being derived from a homogeneous cell type, whether normal or abnormal, as opposed to being from heterogeneous tissue or transformed tissue culture cell lines. Moreover, the cDNAs libraries permit the comparative analysis of mRNA expression during development, aging, neoplastic transformation, etc. The cDNA libraries of the invention, thus, are useful for measuring the simultaneous fluctuations of expression of multiple genes or genetic alterations occurring in developing or diseased tissues.

The present invention has applications in routine diagnosis of human tumors including microdissection of pre-malignant lesions of all types of cancer, genetic analysis of infectious diseases, gene therapy, tissue transformation, and gene localization and analysis of transgenic animals. Additional applications of this technique include analysis of the genotype, cellular products, or infesting organisms of rare populations such as monocytes infected with drug resistant organisms, Reed-Sternberg cells of Hodgkins disease, Kaposi's sarcoma cells, stem cells, and vessel cells. Moreover, genetic analysis, or identification of, micro-organisms infesting microscopically visualized cells in tissues, lymph nodes or inflammatory areas can also be accomplished with high precision.

Although the present invention has been described with reference to particular means, materials and embodiments, one skilled in the art can easily ascertain the essential characteristics of the present invention and various changes, modifications and alterations may be made to adapt the various uses and characteristics without departing from the spirit and broad scope of the present invention as described by the claims which follow.

What is claimed is:

1. A method of direct extraction of cellular material from a tissue sample which comprises:

providing a tissue sample;

providing a slide for mounting of the tissue sample having a first adhesive attraction to the tissue sample;

mounting the tissue sample to the slide;

providing a transfer surface which only upon activation at selected regions has a property to provide the selected regions thereof with adhesive characteristics with a second and greater adhesive attraction to the tissue sample;

juxtaposing the tissue sample with the transfer surface;

identifying at least one portion of the tissue sample which is to be extracted;

activating a region on the transfer surface with radiation so that the selected region of the transfer surface adheres to the at least one portion of the tissue sample while preserving focal tissue morphology;

separating the transfer surface from the tissue sample while maintaining adhesion between the selected region of the transfer surface and the at least one portion of the tissue sample so that the at least one portion of the tissue sample is extracted from a remaining portion of the tissue sample.

2. A method of direct extraction of cellular material from a tissue sample according to claim 1 which comprises:

dipping the provided slide in an aqueous glycerol solution; and, drying the slide before the placing of the tissue sample on the slide.

3. A method of direct extraction of cellular material from a tissue sample according to claim 1 which comprises:

providing an enclosing material having a high bonding strength to the transfer surface;

enclosing the tissue sample in the provided material before placing the tissue sample on the slide.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

CAATACCTGA ACACCTTCTA      20

(2) INFORMATION FOR SEQ ID NO: 2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 2:

GTTCTTGGTC TAGTGTATGT C      21